(12) United States Patent
Schabbach et al.

(10) Patent No.: US 10,391,235 B2
(45) Date of Patent: Aug. 27, 2019

(54) DEVICE AND METHOD FOR DETERMINING INFORMATION RELATED TO A MEDICAL DEVICE

(71) Applicant: Sanofi-Aventis Deutschland GmbH, Frankfurt am Main (DE)

(72) Inventors: Michael Schabbach, Frankfurt am Main (DE); Amit Kohli, Paris (FR)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 270 days.

(21) Appl. No.: 14/791,293

(22) Filed: Jul. 3, 2015

(65) Prior Publication Data

US 2015/0306304 A1    Oct. 29, 2015

Related U.S. Application Data

(63) Continuation of application No. 13/583,948, filed as application No. PCT/EP2011/054283 on Mar. 22, 2011, now Pat. No. 9,125,991.

(30) Foreign Application Priority Data

Mar. 22, 2010 (EP) .................................... 10157233

(51) Int. Cl.
  *A61M 5/14* (2006.01)
  *A61M 5/315* (2006.01)
  (Continued)

(52) U.S. Cl.
  CPC .......... *A61M 5/14* (2013.01); *A61B 5/14532* (2013.01); *A61B 5/4839* (2013.01); *A61M 5/31* (2013.01);
  (Continued)

(58) Field of Classification Search
  CPC .. A61M 2005/3125; A61M 2005/3126; A61M 2205/276; A61M 2205/3306;
  (Continued)

(56) References Cited

U.S. PATENT DOCUMENTS 6,113,578 A     9/2000  Brown
6,482,185 B1 *  11/2002 Hartmann ......... A61M 5/31525
                                                      604/189

(Continued)

FOREIGN PATENT DOCUMENTS

EP         1502614 A2     2/2005
JP         2001-017542    1/2001
(Continued)

OTHER PUBLICATIONS

Form PCT/IPEA/416; Notification of Transmittal of the International Preliminary Report on Patentability.
(Continued)

*Primary Examiner* — Quynh-Nhu H. Vu
(74) *Attorney, Agent, or Firm* — Fish & Richardson P.C.

(57) ABSTRACT

The invention relates to an apparatus (2, 3), comprising a mating unit (20-1, 20-2) for releasably attaching the apparatus (2) to a medical device (1) or for releasably receiving at least a part of the medical device (1). The apparatus (2, 3) further comprises one or more optical sensors (25, 26) and/or one or more acoustical sensors (27) for determining information related to a condition and/or use of the medical device (1). The invention further relates to a system comprising such an apparatus (2, 3) and such a medical device (1), to a method (500, 600, 700) and a computer program (61) for determining information related to a condition and/or use of such a medical device (1), and to a computer-readable medium (60) storing such a computer program (61).

9 Claims, 11 Drawing Sheets

(51) Int. Cl.
*A61M 5/31* (2006.01)
*A61M 5/50* (2006.01)
*G06F 19/00* (2018.01)
*A61B 5/145* (2006.01)
*A61B 5/00* (2006.01)
*G16H 30/20* (2018.01)
*A61B 7/04* (2006.01)
*A61M 5/00* (2006.01)
*A61M 5/20* (2006.01)
*A61M 5/24* (2006.01)

(52) U.S. Cl.
CPC .... *A61M 5/31525* (2013.01); *A61M 5/31533* (2013.01); *A61M 5/5086* (2013.01); *G06F 19/3468* (2013.01); *G16H 30/20* (2018.01); *A61B 7/04* (2013.01); *A61M 5/002* (2013.01); *A61M 5/20* (2013.01); *A61M 5/24* (2013.01); *A61M 2005/3125* (2013.01); *A61M 2005/3126* (2013.01); *A61M 2205/276* (2013.01); *A61M 2205/3306* (2013.01); *A61M 2205/3375* (2013.01); *A61M 2205/3569* (2013.01); *A61M 2205/3592* (2013.01); *A61M 2205/43* (2013.01); *A61M 2205/502* (2013.01); *A61M 2205/52* (2013.01); *A61M 2205/581* (2013.01); *A61M 2205/583* (2013.01); *A61M 2205/6063* (2013.01); *A61M 2205/6081* (2013.01)

(58) Field of Classification Search
CPC .. A61M 2205/3375; A61M 2205/3569; A61M 2205/3592; A61M 2205/43; A61M 2205/502; A61M 2205/52; A61M 2205/581; A61M 2205/583; A61M 2205/6063; A61M 2205/6081; A61M 5/002; A61M 5/14; A61M 5/20; A61M 5/24; A61M 5/31; A61M 5/31525; A61M 5/31533; A61M 5/5086; A61B 5/14532; A61B 5/4839; A61B 7/04; G06F 19/3468
See application file for complete search history.

(56) References Cited

U.S. PATENT DOCUMENTS

| | | |
|---|---|---|
| 2003/0098022 A1 | 5/2003 | Nakao et al. |
| 2004/0097883 A1* | 5/2004 | Roe .................. A61M 5/31541 604/207 |
| 2007/0210157 A1 | 9/2007 | Miller |
| 2009/0069742 A1* | 3/2009 | Larsen ................ A61M 5/315 604/22 |
| 2009/0314292 A1 | 12/2009 | Overfield |
| 2010/0213255 A1 | 8/2010 | Yoo |
| 2011/0313395 A1* | 12/2011 | Krulevitch ............. A61M 5/24 604/504 |
| 2013/0072897 A1 | 3/2013 | Day et al. |

FOREIGN PATENT DOCUMENTS

| | | |
|---|---|---|
| JP | 2001-17542 A | 1/2001 |
| JP | 2007-510469 | 4/2007 |
| KR | 10-2003-0014387 | 2/2003 |
| WO | WO 2005/046559 | 5/2005 |
| WO | 2007107564 A1 | 9/2007 |
| WO | 2009024562 A1 | 2/2009 |

OTHER PUBLICATIONS

English Translation of Abstract of Japanese Patent Application No. 2001-017542 dated Sep. 14, 2017.
International Preliminary Report on Patentability in International Application No. PCT/EP2011/054283, dated May 2, 2012, 18 pages.
International Search Report and Written Opinion in International Application No. PCT/EP2011/054283, dated Jul. 27, 2011, 11 pages.
Extended European Search Report in Application No. 18179403.3, dated Jan. 3, 2019, 12 pages.

* cited by examiner

DEVICE AND METHOD FOR DETERMINING INFORMATION RELATED TO A MEDICAL DEVICE

CROSS REFERENCE TO RELATED APPLICATIONS

The present application is a continuation application of U.S. patent application Ser. No. 13/583,948, filed Feb. 13, 2013, which is a 371 of International Patent Application No. PCT/EP2011/054283, filed Mar. 22, 2011 which claims the benefit of European Patent Application No 10157233.7, filed Mar. 22, 2010 the entire contents of which are incorporated entirely herein by reference.

FIELD OF THE INVENTION

The present invention relates to an apparatus, a method and a computer program for determining information related to a condition and/or use of a medical device, for example a medical device configured to eject a medicament.

BACKGROUND OF THE INVENTION

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a dosage knob and observing the actual dose from a dose window or display of the insulin pen. The dose is then injected by inserting the needle into a suited skin portion and pressing an injection button of the insulin pen.

To be able to monitor insulin injection, for instance to prevent false handling of the insulin pen or to keep track of the doses already applied, it is desirable to measure information related to a condition and/or use of the injection device, such as for instance information on the injected insulin type and dose.

In this respect, international patent publication WO 2009/024562 discloses a medical device with a value sensor. A Radio Frequency Identification (RFID) unit comprises a value sensor such as a pressure sensor and is integrated with a liquid medicament container to enable wireless pressure or other medicament relevant parameter value monitoring. The liquid medicament container is coupled with a first housing part of the medical device, which first housing part may for instance constitute a pre-filled disposable injection device. The RFID unit communicates wirelessly with a control circuit that is contained in a second housing part of the medical device that is releasably attached to the first housing part. The control circuit is adapted to process the values measured by the RFID unit, to compare it with pre-defined values and to provide an alert to the user if the measured values fall outside normal operating conditions, and to communicate data relating to the measured values to an external device for further data processing.

The control circuit of the medical device described in WO 2009/024562 can thus be used with a series of pre-filled disposable injection devices, but the requirement that the RFID unit with the value sensor is contained in the medicament container of the pre-filled disposable injection devices significantly increases the costs of the pre-filled disposable injection device.

SUMMARY OF SOME EMBODIMENTS OF THE INVENTION

It is thus inter alia an object of the present invention to provide an apparatus, a method and a computer program for determining information related to a condition and/or use of a medical device while dispensing with costly measurement components within the medical device.

According to a first aspect of the present invention, an apparatus is disclosed, comprising a mating unit for releasably attaching the apparatus to a medical device or for releasably receiving at least a part of the medical device, and one or more optical sensors and/or one or more acoustical sensors for determining information related to a condition and/or use of the medical device.

According to a second aspect of the present invention, a system is disclosed, comprising a medical device and an apparatus according to the first aspect of the present invention.

According to a third aspect of the present invention, a method is disclosed, comprising determining, based on information captured by one or more optical sensors and/or one or more acoustical sensors, information related to a condition and/or use of a medical device, wherein the sensors are comprised in an apparatus that further comprises a mating unit for releasably attaching the apparatus to the medical device or for releasably receiving at least a part of the medical device.

Accordingly, also an apparatus configured to perform the method according to the third aspect of the present invention shall be considered to be disclosed.

According to a fourth aspect of the present invention, furthermore a computer program is disclosed, comprising program code for performing the method according to the third aspect of the present invention when the computer program is executed on a processor. The computer program may for instance be storable or encodable in a computer-readable medium. The computer program may for instance at least partially represent software and/or firmware of the processor.

According to a fifth aspect of the present invention, furthermore a computer-readable medium is disclosed, having a computer program according to the fourth aspect of the present invention stored thereon. The computer-readable medium may for instance be embodied as an electric, magnetic, electro-magnetic, optic or other storage medium, and may either be a removable medium or a medium that is fixedly installed in an apparatus or device. Non-limiting examples of such a computer-readable medium are a Random-Access Memory (RAM) or a Read-Only Memory (ROM). The computer-readable medium may for instance be a tangible medium, for instance a tangible storage medium. A computer-readable medium is understood to be readable by a computer, such as for instance a processor.

In the following, features and embodiments (exhibiting further features) of the present invention will be described, which are understood to equally apply to the apparatus, system, method, computer program and computer-readable medium of the present invention described above. In particular, a mentioning that a component is configured or arranged to perform a certain action should be understood to also disclose an according method step of the method according to the third aspect of the present invention and an according program code of the computer program according to the fourth aspect of the present invention. These single features/embodiments are considered to be exemplary and non-limiting, and to be respectively combinable independently from other disclosed features/embodiments with the apparatus, system, method, computer program and computer-readable medium of the present invention as described above. Nevertheless, these features/embodiments shall also be considered to be disclosed in all possible combinations with each other and with the apparatus, system, method, computer program and computer-readable medium of the present invention as described above.

The medical device may for instance be configured to eject a medicament (non-limiting examples of a medicament, also frequently referred to as a "drug", are a substance that, when absorbed into the body of a living organism, alters normal bodily function, and a substance used in the treatment, cure, prevention, or diagnosis of disease or used to otherwise enhance physical or mental well-being of a creature). The ejected drug or medicament may for instance be in a solid (e.g. a powder), liquid or gaseous state, or may comprise a mixture of components in solid, liquid and/or gaseous states, such as an aerosol.

The ejected medicament may for instance be at least partially (for instance completely) administered (for instance by way of injection or infusion) into material, e.g. a body of a creature (for instance a human being or an animal). Non-limiting examples of the medical device are thus an injection device (such as an injection pen) or an infusion device (such as an infusion pump). Therein, an injection process may for instance be differentiated from an infusion process inter alia based on the time each process takes (For instance, an injection process may have a significantly smaller duration (e.g. less than 5 minutes) as compared to an infusion process). The administering of the medicament may for instance be executed with the medical device by an entity (a human being or a machine). The human being executing the administering of the medicament may then for instance be a patient receiving the medicament, or another person, such as a member of health personnel, such as doctor or a nurse. An example of a medicament to be administered with the medical device is insulin.

The medical device may for instance be a disposable device that is designed for a limited number of ejection processes and subsequent disposal. The medical device may for instance be pre-filled and non-refillable, so that it has to be disposed after all of or substantially all of the medicament(s) contained therein has been injected. Equally well, the medical device may be equipped with exchangeable containers comprising the medicament to be injected. The medical device may for instance be a pen-shaped injection device with an injection needle at one end and an injection button at the other end.

The apparatus may for instance be a supplementary component with a mating unit via which the apparatus is releasably attachable to the medical device (for instance to an outer surface thereof), for example in a way that the attachment can be released later (for instance by a patient that uses the medical device), in particular without causing damage to the medical device and the apparatus. Non-limiting examples of such a mating unit are components that allow for a form closure, fit closure, screw coupling or Velcro-like coupling between the apparatus and the medical device. For instance, the mating unit be configured to engage with or at least partially embrace the medical device, for instance with one or more arms, clips or rings.

Alternatively, the mating unit of the apparatus may allow releasably receiving at least a part of the medical device, for example in a way that the part of the medical device received by the mating unit can be removed from the mating unit later (for instance by a patient that uses the medical device), in particular without causing damage to the medical device and the apparatus. Non-limiting examples of such a mating unit are a recess or opening of the apparatus into which the medical device can at least partially be inserted or placed.

In both cases, the mating unit may be configured so that the apparatus can be attached to or receive only one type of medical device while excluding other types of medical devices (for instance by providing protrusions on the mating unit that have to engage with corresponding recesses of the medical device or vice versa, with the location of the recesses/protrusions being different for different medical devices), or in such a way that the apparatus can be attached to or receive various types of medical devices.

The apparatus comprises one or more optical/acoustical sensors for determining information related to a condition and/or use of the medical device. The information related to the condition and/or use of the medical device may for instance comprise information related to an ejection of a medicament with the medical device.

The condition of the medical device may for instance comprise characteristics of the medicament contained in the medical device, such as for instance the type of the medicament, the amount of medicament remaining in the medical device and usability of the medicament (e.g. with respect to its expiration date).

The use of the medical device may for instance comprise commissioning or priming of the medical device (for instance when using the medical device for the first time or after a change of a medicament container), preparation of an administering of the medicament (for instance changing a needle, selecting a dose to be ejected), the ejection/administering (e.g. injection) process itself and/or post-ejection/administering tasks (for instance cleaning and needle removal).

The information related to a condition and/or use of the medical device may for instance comprise at least information on the type and/or dose of the medicament that is to be or has been ejected/administered, and/or information on whether an ejection/administering of the medicament has taken place, and/or information on when an ejection/administering of the medicament has taken place.

The sensors are either one or more optical sensors or one or more acoustical sensors. The apparatus may thus comprise one or more optical sensors, one or more acoustical sensors, or both one or more optical sensors and one or more acoustical sensors.

An optical sensor is configured to optically determine information related to a condition and/or use of the medical device. Non-limiting examples of an optical sensor are a camera unit (with or without additional pattern and/or character recognition capability), e.g. for capturing an image of an electronic or non-electronic display of the medical device where the selected medicament dose to be ejected is shown, and a photometer for detecting a colour, e.g. of the medicament or of a container that comprises the medicament.

An acoustical sensor is configured to acoustically determine information related to a condition and/or use of the medical device. Non-limiting examples of an acoustical sensor are a microphone (with or without sound differentiation/recognition capability), e.g. for capturing one or more sounds caused during the use of the medical device.

The information related to the condition and/or use of the medical device may for instance be determined by the optical/acoustical sensor(s) when the apparatus is attached to the medical device or when the part of the medical device is received in the apparatus. This may for instance improve a quality of the determination of the information, for instance by reducing the amount of measurement noise involved in the determination.

According to the present invention, thus information related to a condition and/or use of a medical device is determined by optical/acoustical sensor(s) that are comprised in an apparatus which is configured to be attachable to the medical device or to receive at least a part of the medical device. It is thus not necessary to have sensors within the medical device (for instance in a medicament container thereof) that wirelessly communicate with components outside the medical device. The solution according to the present invention is based on the insight that a plurality of parameters related to the condition and/or use of the medical device can be gathered optically and/or acoustically from outside the medical device, i.e. without a need to intrude into the medical device. The apparatus according to the present invention is thus particularly suited as a supplemental that is attached to the same or different types of off-the-shelf medical devices, for instance medical devices that may be pre-filled, disposable, reusable and/or the like. The medical devices may be purely mechanical medical devices, but may equally comprise electronic components, for instance an electronic display for displaying a medicament dose that has been selected for ejection. The information gathered from the medical device by the sensor(s) may then either be further processed by the apparatus (for instance displayed to a user of the medical device), or communicated to another device.

According to an embodiment of the present invention, the one or more optical sensors comprise at least one optical sensor configured to capture an image of an information-bearing or information-displaying part of the medical device. The at least one optical sensor may for instance be a camera unit. The captured image may for instance be further processed and/or stored by the apparatus, and/or may be provided to another device.

Therein, the apparatus may for instance be configured to recognize characters from the captured image. This may for instance be achieved by Optical Character Recognition (OCR). Then for instance only the recognized characters may be further processed (for instance stored) by the apparatus, or be provided to another device. The determining of the information related to a condition and/or use of the medical device comprises recognizing characters from the captured image. Accordingly, the determined information may for instance relate and/or correspond to the recognized characters (e.g. the determined information at least partially equals or comprises the recognized characters such as numbers representing a dose that is to be ejected/administered with the medical device).

The information-displaying part may for instance be a display via which the medical device indicates a medicament dose that is to be or has been ejected/administered with the medical device. The display may for instance be formed by an opening or transparent part in a housing of the medical device through which dose numbers on a sleeve within the medical device can be viewed, wherein the sleeve is coupled to an ejection mechanism of the medical device. A dose may then for instance be selected by turning the sleeve with a dose button, and the selected dose is then displayed via the opening or transparent part. As a further example, the display may for instance be an electronic display, such as for instance a Liquid Crystal Display (LCD), that displays a selected dose.

The information-bearing part may for instance be a printed, engraved or otherwise provided visible code, which may for instance be indicative of a type and/or an expiration date of a medicament contained in the medical device. This code may for instance be provided on a container that includes the medicament. This code may also be provided on the medical device and may then for instance be indicative of a type and/or expiration date of the medical device.

According to an embodiment of the present invention, the apparatus is configured to capture at least two images of the information-bearing or information-displaying part of the medical device and to only recognize characters from at least one of the at least two captured images if no change between the at least two captured images is detected. Alternatively, the apparatus is configured to capture at least two images of the information-bearing or information-displaying part of the medical device and to only recognize characters from at least one of the at least two captured images if no change between at least two of the at least two captured images is detected within a specified period of time.

For instance, the apparatus is configured to only recognize characters from at least one of the at least two captured images if no change between the at least two captured images is detected. The at least two captured images may for instance be subsequently captured images, for instance a currently captured image and a previously captured image or several previously captured images. Alternatively and/or additionally, the apparatus is configured to only recognize characters from at least one of the at least two captured images if no change between at least two of the at least two captured images is detected within a specified period of time. The at least two images of the at least two captured images may, for instance, be a currently captured image and a previously captured image that was captured immediately before the current image was captured or a previously captured image that was captured after or when the last change between captured images was detected. Also, the apparatus may for instance be configured to only (or additionally) recognize characters from at least one of the captured images if a change between (at least two of) the at least two captured images is detected. Therein, detection of the change may not be based on character recognition. Furthermore, it may for instance be also determined whether or not there is a change in the determined information (e.g. in a specified period of time).

For instance, the currently captured image may be compared to the previously captured image(s) in order to determine or detect (e.g. based on a threshold) whether or not there is a change between the captured images. Therein, the comparison to previously captured images may be limited to the image of the previously captured images that was captured immediately before the current image was captured and/or to the images of the previously captured images that were captured within a first specified (e.g. pre-defined) period of time (e.g. 0.1 seconds) before the current image was captured. For instance, it is monitored (e.g. by performing a time measurement) for how long no change between a currently captured image and a previously captured image is detected. For instance, the currently captured image may be compared to the previously captured images that was captured immediately before the current image was captured and, if, for instance, no change is detected, a new time measurement may be started or an already started time measurement may be maintained, whereas, if, for instance, a change is detected, no time measurement may be started and an already started time measurement may be stopped. Alternatively, for instance, the currently captured image may be compared to the previously captured image that was captured after or when the last change was detected and, if, for instance, a change is detected, a new time measurement may be started and an already started time measurement may be stopped, whereas, if, for instance, no change is detected, an already started time measurement may be maintained.

The comparison may be based on image analysis techniques such as pattern recognition performed on the currently captured image and on the previously captured image(s). For instance, it may be analyzed whether a pattern (such as a scale) of the information-bearing or information-displaying part of the medical device shown on the currently captured image is changed. For instance, it may be searched for patterns in the image(s) that have a certain size and/or aspect ratio and these patterns may be compared with previously saved patterns. In some embodiments, a change may be detected if there is any change between the images, however, in other embodiments, a change may only be detected if at least a specified percentage (e.g. a percentage within 5-50%) of the image between the images changed.

For instance, captured images are only sub-images of the information-bearing or information-displaying part of the medical device. The sub-images may have a low resolution and/or only show a part (such as only a scale and/or characters) of the information-bearing or information-displaying part of the medical device. Alternatively, the captured sub-images may show the entire information-bearing or information-displaying part of the medical device.

For instance, an image of the (entire) information-bearing or information-displaying part of the medical device and/or with a high resolution is only captured to perform a character recognition, if no change between the sub-images is detected (e.g. in the first specified period of time). This is particularly advantageous to reduce the amount of data to be analyzed.

[admin1] For instance, during a dose dialing procedure the selected dose to be ejected/injected by the medical device displayed on the information-bearing or information-displaying part of the medical device may permanently change (e.g. interruptions typically (with a high probability) last less than 0.1 seconds), whereas only the finally selected dose has to be determined. Thus, it is advantageous to only perform the character recognition (and to determine the selected dose) if no change between the previously captured images (e.g. sub-images) is detected within the first specified period of time.

According to an embodiment of the present invention the determining further comprises at least partially monitoring a timing of an application sequence of the medical device.

For instance, the application sequence of the medical device may at least partially be predefined (e.g. the application sequence may comprise mandatory and/or optional steps in a predefined sequence). The steps of the application sequence may for instance be user actions, which have to be performed on the medical device by a user. Exemplary steps of the application sequence of a medical device for ejecting a medicament are:
  performing a safety test such as a priming step,
  dialling/selecting a dose for a medicament that is to be injected/ejected by the medical device,
  correcting the dialed/selected dose, and/or
  injecting/ejecting the dialed/selected dose.

The at least partially monitoring of the timing of the application may for instance comprise monitoring (e.g. measuring) the time difference(s) between different steps of an application sequence of the medical device. For instance, the time difference between the end time of a step of the application sequence and the current time or the start time of a subsequent step of the application sequence may be monitored (e.g. measured). Also, the time difference between the start time and the end time of a step of the application sequence may for instance be monitored (e.g. measured).

The at least partially monitored timing of the application sequence may then, for instance, at least partially be compared with one or more specified periods of time (e.g. the first specified period of time). For instance, the time difference between the end time of dialing a dose (e.g. the last time a dialed dose was changed/a dosage knob was turned) and the current time is monitored and compared to the first specified period of time (e.g. 0.1 seconds). For instance, it is monitored for how long no change between captured images (e.g. subsequently captured images) of the information-bearing or information-displaying part of the medical device is detected. If this monitored time difference, for instance, exceeds the first specified period of time, the character recognition may be performed.

For instance, the monitored timing of the application sequence advantageously allows differentiating (e.g. with a high probability) between an interruption (i.e. a pause) of a step of the application sequence and a termination of a step of the application sequence and/or between two steps of the application sequence such as an ejection during a priming step and an (e.g. longer lasting) ejection during an injection step.

According to an embodiment of the present invention, the apparatus is configured to only determine the information and/or to further process the determined information if the monitored timing at least partially corresponds to a specified (e.g. pre-defined) timing of an application sequence of the medical device. For instance, it is monitored for how long no change between subsequently recognized characters (e.g. subsequently recognized from subsequently captured images) is detected. If this monitored time difference, for instance, exceeds a second specified (e.g. pre-defined) period of time, the currently recognized character may, for instance, at least partially be determined to correspond to the information related to a condition and/or use of the medical device and/or the determined information may be further processed by the apparatus. Thus, the monitored timing may, for instance, confirm (e.g. with a high probability) that a recognized character at least partially corresponds to the information related to a condition and/or use of the medical device. The second specified period of time may be greater, equal or smaller than the first specified period of time.

The recognized character(s) may, for instance, correspond to a selected dose of a medicament that is to be ejected/injected by the medical device and displayed on the information-bearing or information-displaying part of the medical device. For instance, corrections of a selected dose are typically (with a high probability) performed within a second specified period of time (e.g. 3 seconds) after the dose has been dialed. Thus, for instance, the time difference between the end time of dialing a dose (e.g. the last time a dialed dose was changed/a dosage knob was turned) and the current time is monitored and compared to the second specified period of time (3 seconds). If the time difference exceeds the second specified period of time, the recognized character corresponds to the selected dose with a high probability.

Additionally, a user confirmation of the determined information may, for instance, be necessary, for instance to guarantee a correct determination thereof. According to an embodiment of the present invention, the one or more optical sensors may comprise at least one optical sensor configured to capture information representative of a colour of at least a part of the medical device or to determine a colour of at least a part of the medical device. The at least one optical sensor may for instance be a photometer, for instance a spectral photometer. Alternatively, the optical sensor may for instance be a camera unit, for instance the same camera unit that is used for capturing the image of the information-bearing or information-displaying part of the medical device. The captured information representative of the colour or the determined colour may for instance be further processed and/or stored by the apparatus, and/or may be provided to another device.

In case that the at least one optical sensor is configured to capture the information representative of the colour of at least a part of the medical device, the apparatus may for instance be configured to recognize a colour of the part of the medical device from the captured information. The colour recognition may for instance be based on a recognition of grey patterns in a monochrome black-white-picture (wherein different grey patterns may for instance be associated with different colours to be recognized).

According to an embodiment of the present invention, the one or more acoustical sensors may comprise at least one acoustical sensor configured to capture a sound produced when the medical device is used. The sound may for instance be produced by the medical device (or part thereof) mechanically, for instance when components of the medical device are moved with respect to each other (e.g. a clicking sound), but the sound may also be produced by the medical device electronically, for instance to indicate a certain status of the medical device (e.g. that the medicament ejection/administering is finished or that the medical device is ready for the ejection/administering).

Therein, the apparatus may for instance be configured to differentiate at least two different sounds produced by the device. For instance, a sound produced when dialling a dose may be differentiated from a sound produced when a medicament dose is ejected. Furthermore, an ejection sound produced when performing a prime shot (without injecting the medicament into a creature) may be differentiated acoustically from an ejection sound produced when an actual injection into a creature is performed.

Therein, the apparatus may for instance be configured to recognize, from the captured sound, at least an ejection of a medicament performed with the medical device. Recognition of the ejection of the medicament may for instance trigger the apparatus to perform an action, for instance to capture an image of an information-bearing or information-displaying part of the medical device, based on which image then for instance the dose of the ejected medicament may be determined, or to store, process and/or transmit a captured image of an information-bearing or information-displaying part of the medical device or information relating to such a captured image. This captured image may for instance be the last image that was captured (in a regular or irregular series of image captures) before the ejection of the medicament. This recognition may also or alternatively trigger transmission of information captured by the optical/acoustical sensors to another device.

According to an embodiment of the present invention, the apparatus is configured to only capture an image of the information-bearing or information-displaying part of the medical device and/or to perform the recognizing characters if the captured sound corresponds to a sound produced when a dose for a medicament to be ejected by the medical device is dialed. The sound may for instance be a sound produced mechanically such as a clicking sound and/or a sound produced electronically. Alternatively and/or additionally, the apparatus may for instance be configured to capture a picture at least partially independently of a captured sound (e.g. at least one picture per specified time interval). Furthermore, it may for instance be also determined whether or not there is a change in the determined information (e.g. in a specified period of time).

The information related to a condition and/or use of the medical device may for instance be determined by capturing an image of an information-bearing or information-displaying part of the medical device as described above. The captured image may for instance be further processed and/or stored by the apparatus, and/or may be provided to another device. Therein, the apparatus may for instance be configured to recognize characters from the captured image.

This embodiment may be advantageous, because real-time detection of a sound produced when the medical device may be used is less energy consuming than, for instance, permanently capturing an image to detect a change in the captured image(s), for instance showing an information-bearing or information-displaying part of the medical device.

According to an embodiment of the present invention, the apparatus may further comprise a display unit for displaying information representative of at least a part of the determined information (e.g. information on a dose of the medicament that is to be or has been selected). The display unit may for instance be an electronic display such as a Liquid Crystal Display (LCD), an Organic Light Emitting Diode (OLED) display, and/or the like. In an example embodiment, the information shown on the display unit may continuously be updated to show the currently selected dose during dose dialing. The display unit may further show the ejected dose after ejection. The display unit may show additional information, for example a current time, the time since the last ejection/administering, and/or the like. The display unit may for instance be advantageous since a display of the medical device (e.g. a display via which the dose of the medicament that is to be or has been ejected is indicated) may at least partially be covered by one or more optical sensors of the apparatus, so that it may be advantageous to provide optical feedback to the user via the display unit when the user dials a dose.

According to an embodiment of the present invention, the apparatus may further comprise an interface configured to provide the determined information to another device via a wired or wireless connection. The interface may for instance be a standardized interface such as for instance a Universal Serial Bus (USB) or a Bluetooth interface, but may equally well be a proprietary interface. The wireless connection may for instance be based on radio waves, optical waves, sound waves, but also on magnetic or electric fields.

Therein, the other device receiving the information may for instance be configured to store the information, for instance in the form of a logbook or archive, and/or to use the information to monitor use of the medical device (for instance to launch an alert if improper handling of the medical device is detected), and/or to use the information (and potentially further information) to determine a proposal of the next type and/or dose of medicament to be administered. In an example embodiment, such information may be provided back to the medical device and may optionally be displayed to a user of the medical device.

The other device may for instance be a blood glucose monitoring system, which may for instance reveal individual patterns of blood glucose changes and may help in the planning of meals, activities, and at what time of day to take medicaments or to administer a medicament.

The blood glucose monitoring system may for instance comprise a blood glucose meter for measuring the blood glucose level of the patient that uses the medical device, or may (for instance regularly or irregularly) receive information on this blood glucose level from a blood glucose meter. The blood glucose meter may for instance measure the blood glucose level based on a drop of blood placed on a disposable test strip which interfaces with a digital meter.

Provision of the information determined by the one or more sensors of the apparatus may be triggered by a user (e.g. by pushing a button) or automatically, for instance in response to a detection that a medicament dose is or has been ejected.

According to an embodiment of the present invention, the apparatus may further comprise an interface configured to receive information indicative of a type and/or dose of medicament to be ejected. Such information may for instance be received from a monitoring system, such as for instance a blood glucose monitoring system as described above.

Therein, the apparatus may then for instance further comprise a display unit for displaying the received information indicative of the type and/or dose of medicament to be ejected. This display unit may for instance be the same display on which the information determined by the optical/acoustical sensor(s) of the apparatus are displayed, or another display unit.

Therein, the apparatus may for instance further comprise a controller for controlling if a type and/or dose of medicament selected for ejection at the medical device matches the type and/or dose of medicament to be ejected as indicated by the received information. This contributes to avoid application of inaccurate doses. For instance, if a mismatch is detected, a warning or alert signal may be issued by the apparatus.

According to an embodiment of the present invention, the apparatus may further comprise a processor for determining a proposal of a type and/or dose of medicament to be ejected (for instance ejected to be injected into a creature). This proposal may for instance at least be based on information on at least one previously ejected medicament dose, which is stored in the apparatus. The proposal may for instance further be based on one or more parameters (e.g. a blood glucose level) measured from a creature (e.g. a patient) that is to receive the medicament (e.g. via injection or infusion). Information representative of the one or more parameters may for instance be received via a user interface of the apparatus (for instance entered by the user of the medical device), or measured by the apparatus (for instance by a blood glucose meter comprised in or connected to the apparatus), or received via an interface (e.g. by means of a wired or wireless connection).

The apparatus may then for instance implement or comprise a blood glucose monitoring system.

According to an embodiment of the present invention, the apparatus may further comprise a measurement unit for measuring at least one parameter that is representative of a condition of a creature (e.g. a patient) that is to receive a medicament ejectable by the medical device. The at least one parameter may for instance be relevant for determining a type and/or dose of the medicament to be received by the creature.

The at least one parameter may for instance be a blood glucose level. The measurement unit may then for instance be a blood glucose meter, and may for instance comprise an opening for receiving a carrier (e.g. a strip) with a drop of blood of the creature.

According to an embodiment of the present invention, the apparatus may further comprise an acoustical signal generator for producing acoustical signals related to the condition and/or use of the medical device. Said acoustical signal generator may for instance be embodied as a loudspeaker or buzzer. It may for instance produce a feedback and/or warning signal.

According to an embodiment of the present invention, a user of the medical device is required to comfim said determined information (e.b. by performing a confirming action, such as for instance pressing a button of the apparatus). For instance, the determined information is only stored and/or further processed if the user confirms the determined information as correct. Otherwise, the determined information may be corrected (e.g. by the user) and the corrected determined information may then be stored and/or further processed. If the determined is neither comfirmed nor corrected it may, for instance, be discarded.

Only a confirmation by a user may be versatile enough to cover many possible actions of the user during an application sequence and to avoid the storage/further processing of incorrectly determined information.

According to an embodiment of the present invention, the apparatus is configured to determine the information at least partially from recognized characters (e.g. characters recognized from at least one image captured from the information-bearing or information-displaying part of the medical device). Accordingly, the determined information may for instance relate and/or correspond to the recognized characters (e.g. the determined information at least partially equals or comprises the recognized characters such as numbers representing a dose that is to be ejected/administered with the medical device). This may, for instance, advantageously allow to reduce the amount of data corresponding to (e.g. representing) the determined information.

According to an embodiment of the third aspect of the present invention, the method further comprises receiving the information captured by the one or more optical sensors and/or the one or more acoustical sensors. Said optical/acoustical sensors and a unit that performs the determining may for instance be different components of an apparatus, but may equally well at least partially be performed by the same component or components of an apparatus.

According to an embodiment of the third aspect of the present invention, the method further comprises displaying information representative of at least a part of the information related to the a condition and/or use of the medical device.

According to an embodiment of the third aspect of the present invention, the method further comprises providing information representative of at least a part of the information related to the condition and/or use of the medical device to another device via a wired or wireless connection.

According to an embodiment of the third aspect of the present invention, the one or more optical sensors comprise at least one optical sensor configured to capture an image of an information-bearing or information-displaying part of the medical device.

Said determining may then for instance comprise recognizing characters from the captured image.

According to an embodiment of the third aspect of the present invention, the one or more optical sensors comprise at least one optical sensor configured to capture information representative of a colour of at least a part of the medical device or to determine a colour of at least a part of the medical device.

Said determining may then for instance comprise recognizing a colour from the captured information.

According to an embodiment of the third aspect of the present invention, the one or more acoustical sensors comprise at least one acoustical sensor configured to capture a sound produced when the medical device is used.

Said determining may then for instance comprise recognizing, from the captured sound, at least an ejection of a medicament performed with the medical device.

These and further concepts of the invention will be apparent from and elucidated with reference to the detailed description presented hereinafter.

DETAILED DESCRIPTION OF SOME EMBODIMENTS OF THE INVENTION

In the following, embodiments of the present invention will be described with reference to an insulin injection device. The present invention is however not limited to such application and may equally well be deployed with injection devices that eject other medicaments, or with other types of medical devices.

Figure 1:
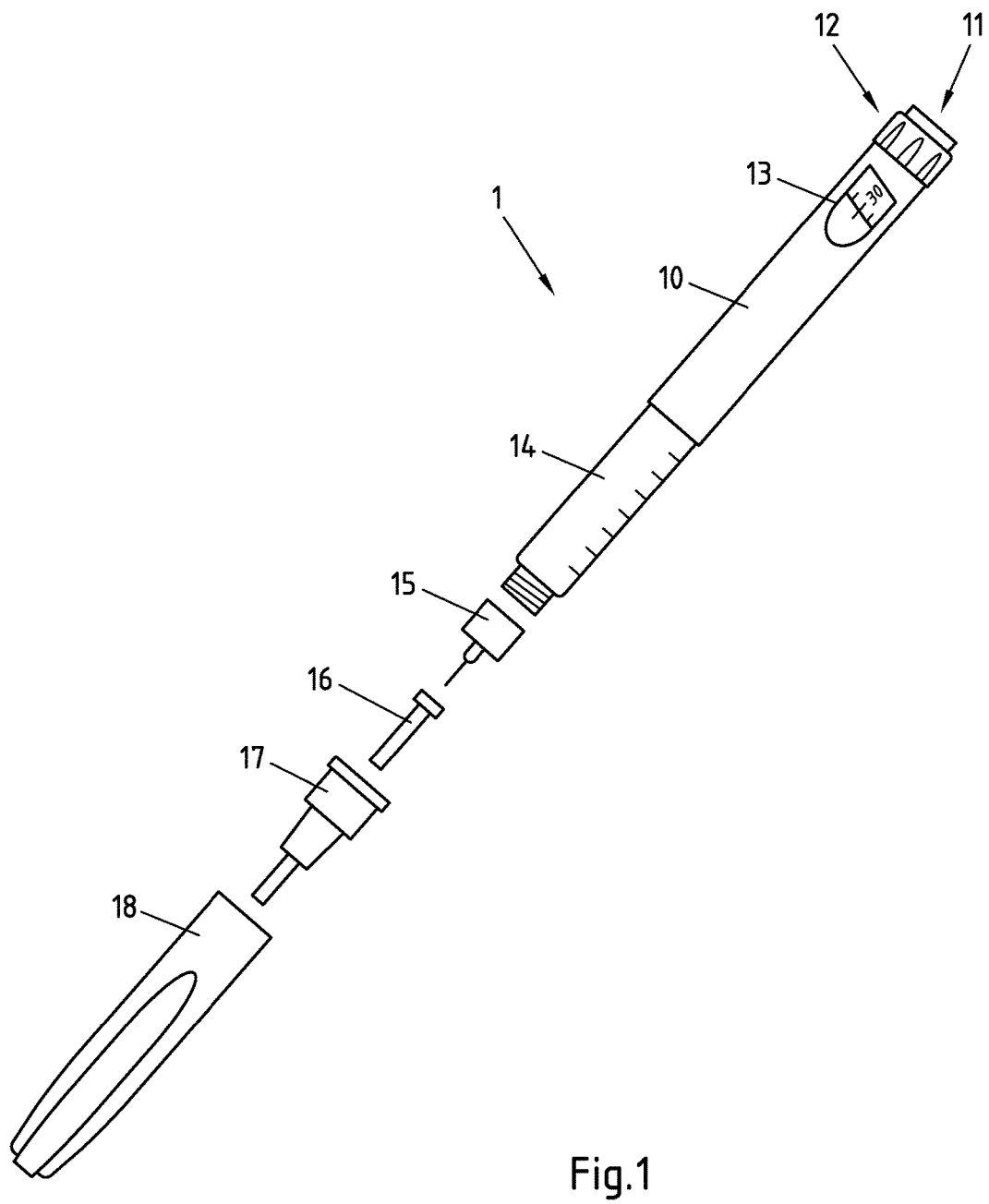
FIG. 1: An exploded view of an injection device.

FIG. 1 is an exploded view of an injection device 1, which may for instance represent Applicant's Solostar® insulin injection pen.

Injection device 1 of FIG. 1 is a pre-filled, disposable injection pen that comprises a housing 10 and contains an insulin container 14, to which a needle 15 can be affixed. The needle is protected by an inner needle cap 16 and an outer needle cap 17, which in turn can be covered by a cap 18.

An insulin dose to be ejected from injection device 1 can be selected by turning the dosage knob 12, and the selected dose is then displayed via dosage window 13, for instance in multiples of so-called International Units (IU), wherein one IU is the biological equivalent of about 45.5 µg pure crystalline insulin (1/22 mg). An example of a selected dose displayed in dosage window 13 may for instance be 30 IUs, as shown in FIG. 1. It should be noted that the selected dose may equally well be displayed differently, for instance by means of an electronic display.

Turning the dosage knob 12 causes a mechanical click sound to provide acoustical feedback to a user. The numbers displayed in dosage window 13 are printed on a sleeve that is contained in housing 10 and mechanically interacts with a piston in insulin container 14. When needle 15 is stuck into a skin portion of a patient, and then injection button 11 is pushed, the insulin dose displayed in display window 13 will be ejected from injection device 1. When the needle 15 of injection device 1 remains for a certain time in the skin portion after the injection button 11 is pushed, a high percentage of the dose is actually injected into the patient's body. Ejection of the insulin dose also causes a mechanical click sound, which is however different from the sounds produced when using dosage knob 12.

Injection device 1 may be used for several injection processes until either insulin container 14 is empty or the expiration date of injection device 1 (e.g. 28 days after the first use) is reached.

Furthermore, before using injection device 1 for the first time, it may be necessary to perform a so-called "prime shot" to remove air from insulin container 14 and needle 15, for instance by selecting two units of insulin and pressing injection button 11 while holding injection device 1 with the needle 15 upwards.

For simplicity of presentation, in the following, it will be exemplarily assumed that the ejected doses substantially correspond to the injected doses, so that, for instance when making a proposal for a dose to be injected next, this dose equals the dose that has to ejected by the injection device. Nevertheless, differences (e.g. losses) between the ejected doses and the injected doses may of course be taken into account.

Figure 2A:
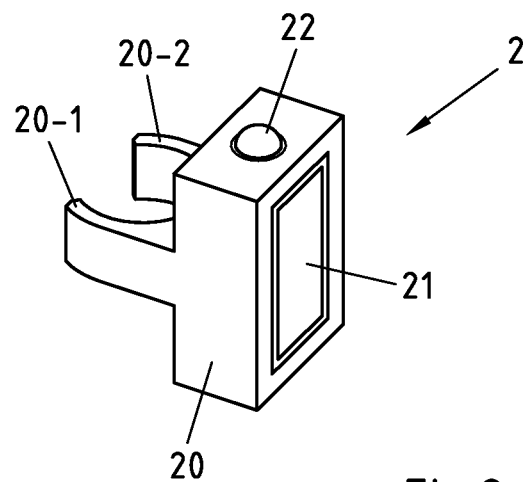
FIG. 2a: a schematic illustration of a supplementary device to be releasably attached to the injection device of FIG. 1 according to an embodiment of the present invention.

FIG. 2a is a schematic illustration of an embodiment of a supplementary device 2 to be releasably attached to injection device 1 of FIG. 1. Supplementary device 2 comprises a housing 20 with two clips 20-1 and 20-2 that function as a mating unit configured and embrace the housing 10 of injection device 1 of FIG. 1, so that supplementary device 2 sits tightly on housing 10 of injection device 1, but is nevertheless removable from injection device 1, for instance when injection device 1 is empty and has to be replaced. Alternatively, the clips 20-1 and 20-2 may for instance be replaced by a ring-shaped member, into which the upper portion of housing 10 of injection device 10 may be inserted so that a tight fit of supplementary device 2 on housing 10 of injection device 1 is achieved. Supplementary device 2 contains optical and acoustical sensors for gathering information from injection device 1. At least a part of this information, for instance a selected dose (and optionally a unit of this dose), is displayed via display unit 21 of supplementary device 2, which accounts for the fact that dosage window 13 of injection device 1 may at least partially be obstructed by supplementary device 2 when being attached to injection device 1. Supplementary device 2 further comprises a button 22, for instance to turn on/off supplementary device 2, and/or to trigger actions (for instance to cause establishment of a connection to another device, and/or to trigger transmission of information from supplementary device 2 to another device, e.g. a blood glucose monitoring system, and/or to cause calculation of a next dose). As will be explained in more detail below, the functionality of such a blood glucose monitoring system and/or the functionality of a blood glucose meter may also be provided by supplementary device 2.

Figure 2B:
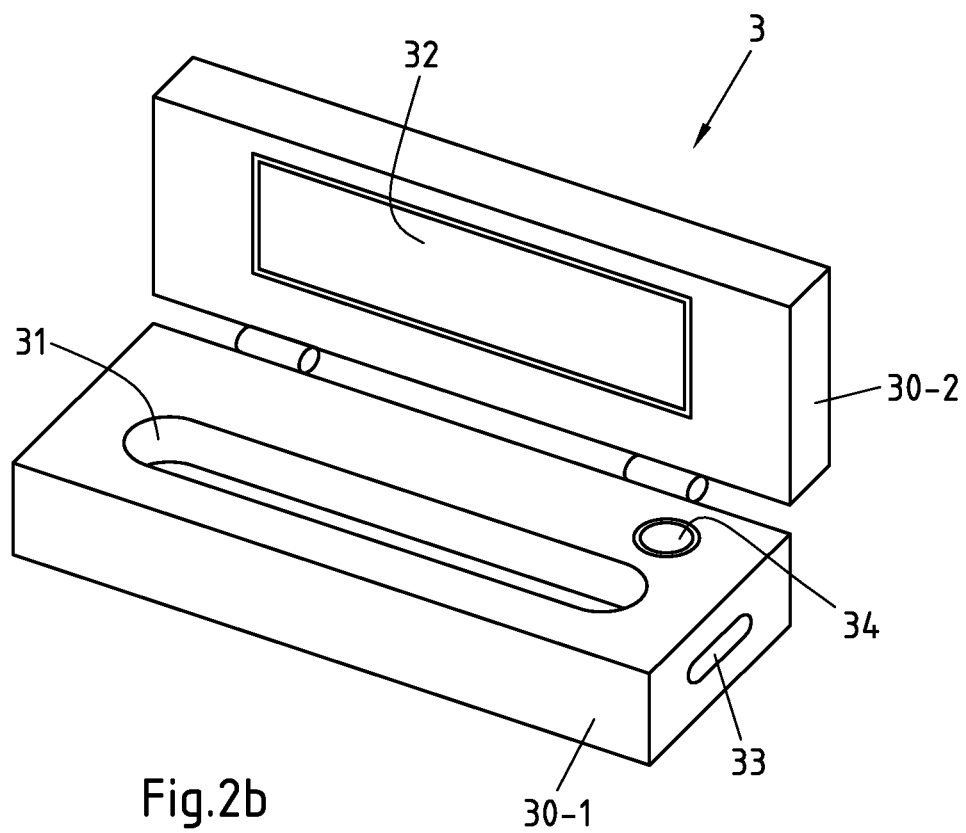
FIG. 2b: a schematic illustration of a supplementary device configured to at least partially receive the injection device of FIG. 1 according to an embodiment of the present invention.

FIG. 2b shows an alternative embodiment of a supplementary device 3 that is configured to at least partially receive the injection device 1 of FIG. 1. Supplementary device 3 comprises a lower part 30-1 and an upper part 30-2 that are connected to each other via hinges so that lower part 30-1 and upper part 30-2 can be collapsed to form a case.

Lower part 30-1 comprises a mating unit that is formed as a recess 31 and is configured to receive injection device 1. When injection device 1 is placed into recess 31, optical and/or acoustical sensors comprised in supplementary device 3 can gather information from injection device 1. At least a part of this information, for instance a selected dose, can be displayed via display unit 32 of supplementary device 3. A use case of supplementary device 3 may for instance be that a user (which may be the patient receiving that is to receive the injection or another person) of injection device 1 selects a dose by turning dosage knob 12 of injection device 1 and then, before performing the injection, places injection device 1 into recess 31 of supplementary device 3. After optical recognition of the selected dose, which may for instance be indicated by displaying the dose on display 32 and/or producing an electronic sound on an acoustical signal generator, the user may then remove injection device 1 from the recess 31 and perform the actual injection. A click sound caused by injection device 1 when the ejection (which in the exemplary case of the medical device being an injection pen coincides with the injection) is performed may also be sensed by an acoustical sensor of supplementary device 3 and may serve as an acknowledgement that the recognized dose has actually been ejected/injected. After the ejection/injection has been performed, the injection device 1 can be stored in recess 31 of supplementary device 3. Supplementary device 3 may thus also serve as storage container for injection device 1, and may be configured accordingly to ensure that quality of the injection device 1 and the insulin contained therein does not deteriorate even when supplementary device 3 is carried around.

Supplementary device 3 also comprises a button 34, for instance to turn on/off supplementary device 3, and/or to trigger actions (for instance to cause transmission of information from supplementary device 2 to another device, e.g. a blood glucose monitoring system, or to cause calculation of a next dose).

In FIG. 2b, furthermore an optional slot 33 is shown, via which supplementary device 3 may receive carrier material (e.g. strips) with drops of blood, which may then be processed by an optional blood glucose meter in order to determine a current blood glucose level of a patient.

Supplementary device 3 may furthermore implement functionality of a blood glucose monitoring system.

FIGS. 3a-3d show various possible distributions of functions among devices when using a supplementary device (such as the supplementary devices of FIGS. 2a and 2b) together with an injection device.

Figure 3A:
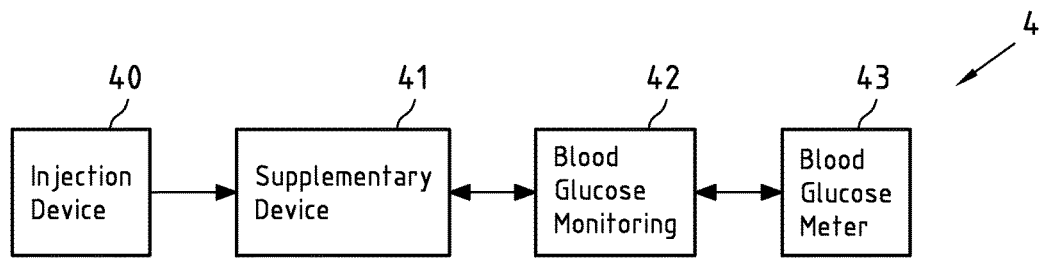
FIG. 3a: a distribution of functions among devices according to an embodiment of the present invention.

In constellation 4 of FIG. 3a, the supplementary device 41 (such as the supplementary devices of FIGS. 2a and 2b) determines information from injection device 40, and provides this information (e.g. type and/or dose of the medicament to be injected) to a blood glucose monitoring system 42 (e.g. via a wired or wireless connection).

Blood glucose monitoring system 42 (which may for instance be embodied as computer, personal digital assistant or mobile phone) keeps a record of the injections a patient has received so far (based on the ejected doses, for instance by assuming that the ejected doses and the injected doses are the same, or by determining the injected doses based on the ejected doses, for instance be assuming that a pre-defined percentage of the ejected dose is not completely received by the patient), and may for instance propose a type and/or dose of insulin for the next injection for this patient. This proposal may be based on information on one or more past injections received by the patient, and on a current blood glucose level, that is measured by blood glucose meter 43 and provided (e.g. via a wired or wireless connection) to blood glucose monitoring system 42.

Therein, blood glucose meter 43 may be embodied as a separate device that is configured to receive a small blood probe (for instance on a carrier material) of a patient and to determine the blood glucose level of the patient based on this blood probe. Blood glucose meter 43 may however also be a device that is at least temporarily implanted into the patient, for instance in the patient's eye or beneath the skin.

The proposed type and/or dose of insulin may be provided from blood glucose monitoring system 42 to supplementary device 41, where it may for instance be displayed to the user of injection device 40 and/or used to check if it matches a dose that is then injected into the patient. Mismatches may for instance trigger warning or alarm signals.

Figure 3B:
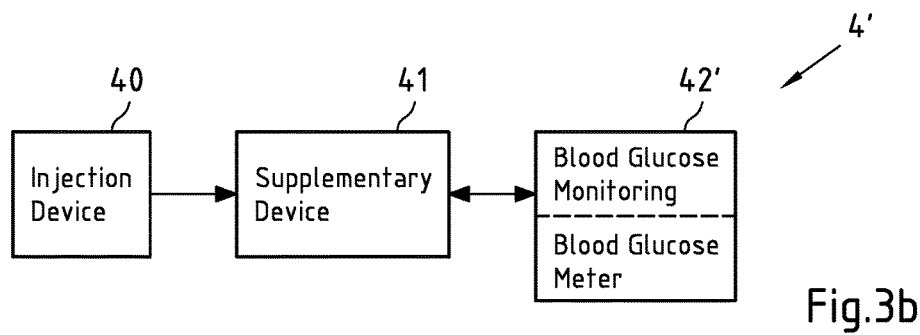
FIG. 3b: a further distribution of functions among devices according to an embodiment of the present invention.

FIG. 3b is a modified constellation 4' where the blood glucose meter 43 of FIG. 3a has been included into blood glucose monitoring system 42 of FIG. 3a, thus yielding the modified blood glucose monitoring system 42' of FIG. 3b. The functionality of injection device 40 and 41 of FIG. 3a is not affected by this modification. Also the functionality of blood glucose monitoring system 42 and blood glucose meter 43 combined into blood glucose monitoring system 42' are basically unchanged, apart from the fact that both are now comprised in the same device, so that wired or wireless communication between these devices is no longer necessary. However, communication between blood glucose monitoring system 42 and blood glucose meter 43 takes place within system 42'.

Figure 3C:
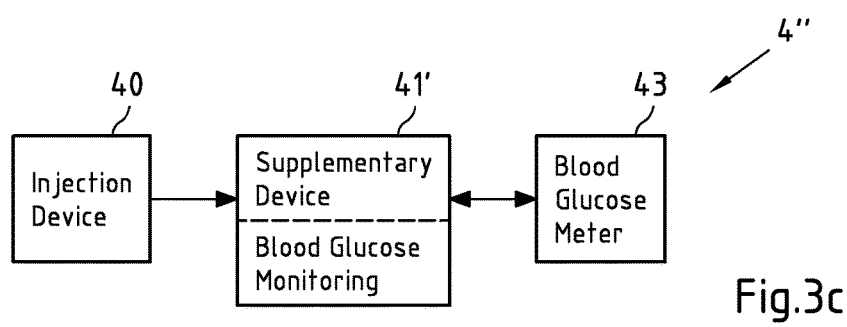
FIG. 3c: a further distribution of functions among devices according to an embodiment of the present invention.

FIG. 3c is another modified constellation 4", where the functionality of the blood glucose monitoring system 42 of FIG. 3a has been included into supplementary device 41 of FIG. 3a, yielding a modified supplementary device 41'. Injection device 40 and blood glucose meter 43 are basically not affected by this modification, apart from the fact that blood glucose meter 43 now communicates with a combined unit 41'.

Figure 3D:
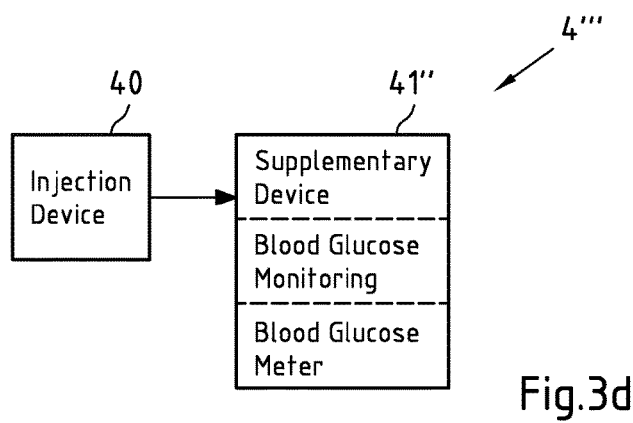
FIG. 3d: a further distribution of functions among devices according to an embodiment of the present invention.

FIG. 3d shows another modified constellation 4''', where the functionality of the blood glucose monitoring system 42 and of the blood glucose meter 43 of FIG. 3a has been included into the supplementary device 41 of FIG. 3a, thus yielding a modified supplementary device 41". Modified supplementary device 41″ is thus capable of measuring a blood glucose level of a patient, to perform blood glucose monitoring, and to read information from the injection device 40. Modified supplementary device 41″ thus may be understood to comprise a supplementary device part, a blood glucose monitoring part, and a blood glucose meter part. The blood glucose monitoring part may then use the information read from the injection device 1 (by the supplementary device part) and measured by the blood glucose meter part. Proposals for next doses to be taken may then be displayed and/or checked against the doses actually injected with injection device 1.

Figure 4:
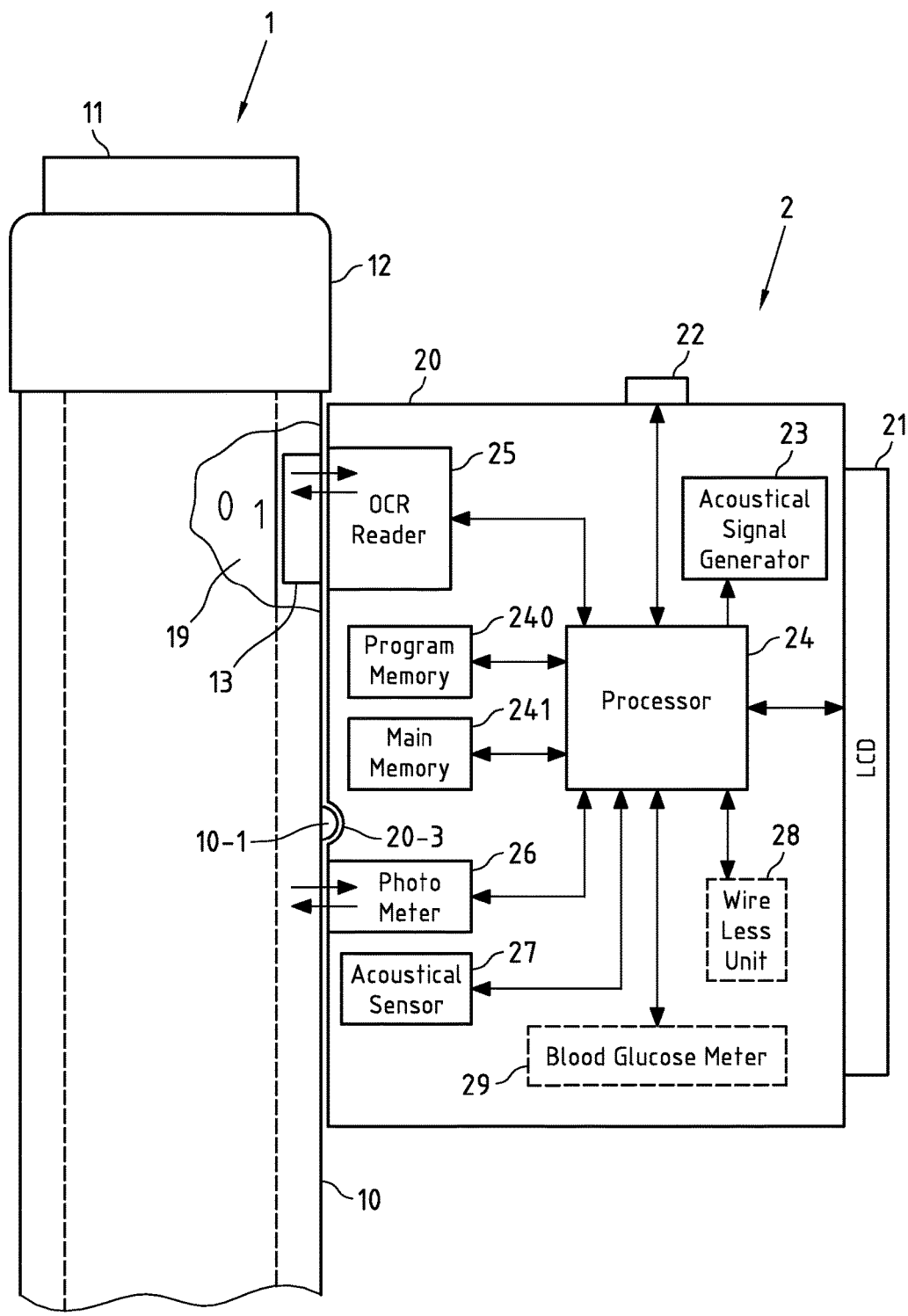
FIG. 4: a schematic view of the supplementary device of FIG. 2a in a state where it is attached to the injection device of FIG. 1.

FIG. 4 shows a schematic view of the supplementary device 2 of FIG. 2a in a state where it is attached to injection device 1 of FIG. 1.

With the housing 20 of supplementary device 2, a plurality of components are comprised, which are controlled by a processor 24, which may for instance be a microprocessor, a Digital Signal Processor (DSP), Application Specific Integrated Circuit (ASIC), Field Programmable Gate Array (FPGA) or the like. Processor 24 executes program code (e.g. software or firmware) stored in a program memory 240, and uses a main memory 241, for instance to store intermediate results. Main memory 241 may also be used to store a logbook on performed ejections/injections and information required to determine a proposal for a next ejection/injection. Program memory 240 may for instance be a Read-Only Memory (ROM), and main memory may for instance be a Random Access Memory (RAM).

In an example embodiment, processor 24 interacts with a button 22, via which supplementary device 2 may for instance be turned on and off. Button 22 may also be used to trigger further actions, for instance to trigger establishment of a connection to another device, or to trigger a transmission of information to another device, or to acknowledge information presented to a user of supplementary device 2.

Processor 24 controls a display unit 21, which is presently embodied as a Liquid Crystal Display (LCD). Display unit 21 is used to display information to a user of supplementary device 2, for instance on present settings of injection device 1, or on a next injection to be given. Display unit 21 may also be embodied as a touch-screen display, for instance to receive user input.

Processor 24 also controls an optical sensor 25, which is presently embodied as an Optical Character Recognition (OCR) reader, that is capable of capturing images of the dosage window 13, in which a currently selected dose is displayed (by means of numbers printed on the sleeve 19 contained in injection device 1, which numbers are visible through the dosage window 13). OCR reader 25 is further capable of recognizing characters (e.g. numbers) from the captured image and to provide this information to processor 24. Alternatively, unit 25 in supplementary device 2 may only be an optical sensor for capturing images and providing information on the captured images to processor 24. Then either processor 24 or a device to which this information is transmitted by supplementary device 2 may be responsible for performing OCR on the captured images. The latter approach may allow reducing the complexity of the supplementary device 2.

Optionally, processor 24 also controls light-sources such as light emitting diodes (LEDs) (e.g. white and/or coloured LEDs), which may be used to illuminate the dosage window 13, in which a currently selected dose is displayed. Due to light potentially reflecting off the surface of a transparent part of the injection device, a diffuser may be used in front of the light-sources, for instance a diffuser made from a piece of acrylic glass. Furthermore, the optical sensor may optionally comprise a lens (e.g. an aspheric lens) leading to a magnification (e.g. a magnification of more than 3:1).

Processor 24 further controls a photometer 26, that is configured to determine an optical property of the housing 10 of injection device 1, for example a colour or a shading. The optical property may only be present in a specific portion of housing 10, for example a colour or colour coding of sleeve 19 or of an insulin container comprised within injection device 1, which colour or colour coding may for instance be visible through a further window in housing 10 (and/or in sleeve 19). Information on this colour is then provided to processor 24, which may then determine the type of injection device 1 or the type of insulin contained in injection device 1 (e.g. SoloStar Lantus with purple colour and SoloStar Apidra with blue colour). Alternatively, a camera unit may be used instead of photometer 26, and an image of the housing, sleeve or insulin container may then be provided to processor 24 to determine the colour of the housing, sleeve or insulin container by means of image processing. Further, one or more light sources may be provided to improve reading of OCR reader 25 and/or photometer 26.

The light source may provide light of a certain wavelength or spectrum to improve colour detection by photometer 26. The light source may be arranged in such a way that unwanted reflections, for example by dosage window 13, are avoided or reduced.

In an example embodiment, instead of or in addition to photometer 26, a camera unit may be deployed to detect a code (for instance a bar code, which may for instance be a one- or two-dimensional bar code) related to the injection device and/or the medicament contained therein. This code may for instance be located on the housing 10 or on a medicament container contained in injection device 1, to name but a few examples. This code may for instance indicate a type of the injection device and/or the medicament, and/or further properties (for instance a expiration date).

Processor 24 further controls (and/or receives signals from) an acoustic sensor 27, which is configured to sense sounds produced by injection device 1. Such sounds may for instance occur when a dose is dialed by turning dosage knob 12 and/or when a dose is ejected/injected by pressing injection button 11, and/or when a prime shot is performed. These actions are mechanically similar but nevertheless sound differently (this may also be the case for electronic sounds that indicate these actions). Either the acoustic sensor 27 and/or processor 24 may be configured to differentiate these different sounds, for instance to be able to safely recognize that an injection has taken place (rather than a prime shot only). A sound captured by acoustic sensor 27 may also be provided to another device that then performs the sound recognition. This may again reduce the complexity of supplementary device 2.

Processor 24 further controls an acoustical signal generator 23, which is configured to produce acoustical signals that may for instance be related to the operating status of injection device 1, for instance as feedback to the user. For example, an acoustical signal may be launched by acoustical signal generator 23 as a reminder for the next dose to be injected or as a warning signal, for instance in case of misuse. Acoustical signal generator may for instance be embodied as a buzzer or loudspeaker. In addition to or as an alternative to acoustical signal generator 23, also a haptic signal generator may be used to provide haptic feedback, for instance by means of vibration.

In an example embodiment, processor 24 controls a wireless unit 28, which is configured to transmit and/or receive information to/from another device in a wireless fashion. Such transmission may for instance be based on radio transmission or optical transmission. Alternatively, wireless unit 28 may be substituted or complemented by a wired unit configured to transmit and/or receive information to/from another device in a wire-bound fashion, for instance via a cable or fibre connection. Such units for wireless or wire-bound transmission/reception may for instance be dispensed with in scenarios as depicted in FIG. 3d, where supplementary device 41''' implements blood glucose monitoring system functionality and also implements a blood glucose meter. When data is transmitted, the units of the data (values) transferred may be explicitly or implicitly defined. For instance, in case of an insulin dose, always International Units (IU) may be used, or otherwise, the used unit may be transferred explicitly, for instance in coded form.

Finally, supplementary device 2 also comprises an optional blood glucose meter 29, which is configured to receive a blood probe (e.g. on a carrier such as a strip) of a patient that is to receive an injection and to determine a blood glucose level therefrom, which then is provided to processor 24 for further processing, for instance to determine a proposal for a type and/or dose of an injection to be applied next.

The supplementary device 2 of FIG. 4 is thus capable of determining information related to a condition and/or use of injection device 1. This information may be either processed by supplementary device 2 itself, or may at least partially be provided to another device (e.g. a blood glucose monitoring system).

As a further detail, FIG. 4 shows a recess 20-3 formed on the housing 20 of supplementary device 2, which recess is configured to receive a key 10-3 formed at a specific position on housing 10 of injection device 1, when supplementary device 2 is attached to injection device 1. This recess-key pair may for instance be arranged to ensure that supplementary device 2 can only be attached to a specific type of injection device 1, for instance to ensure compatibility. Different types of injection devices 1 may for instance use different positions of key 10-1 and/or different forms of key 10-1 to ensure that only compatible supplementary devices 2 are used. Alternatively, such key-recess pairs may be dispensed with, to allow that supplementary device 2 can be used with a variety of different injection devices 1. Supplementary device 2 may then for instance be configured to function with a broad range of injection devices 1. Specifics of single injection devices 1 may nevertheless be taken into account, for instance by recognizing different types of injection devices 1, for instance based on codes or colours that are characteristic of the different types of injection devices 1. Such codes or colours may be sensed by the supplementary device 1 optically in a similar fashion as already explained above, i.e. based on OCR and/or colour recognition (and subsequent comparison of the recognized values (colours with a table).

It should be noted that the functional components of supplementary device 2 as shown in FIG. 4 may equally be present and function in the same way in supplementary device 3 of FIG. 2b.

Figure 5A:
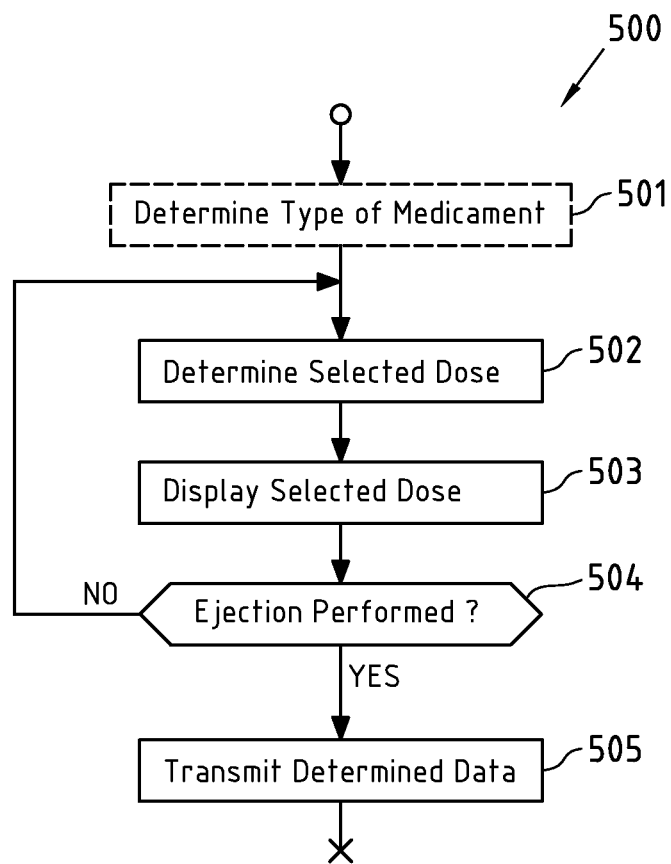
FIG. 5a: a flowchart of an embodiment of a method according to the present invention.
Figure 5B:
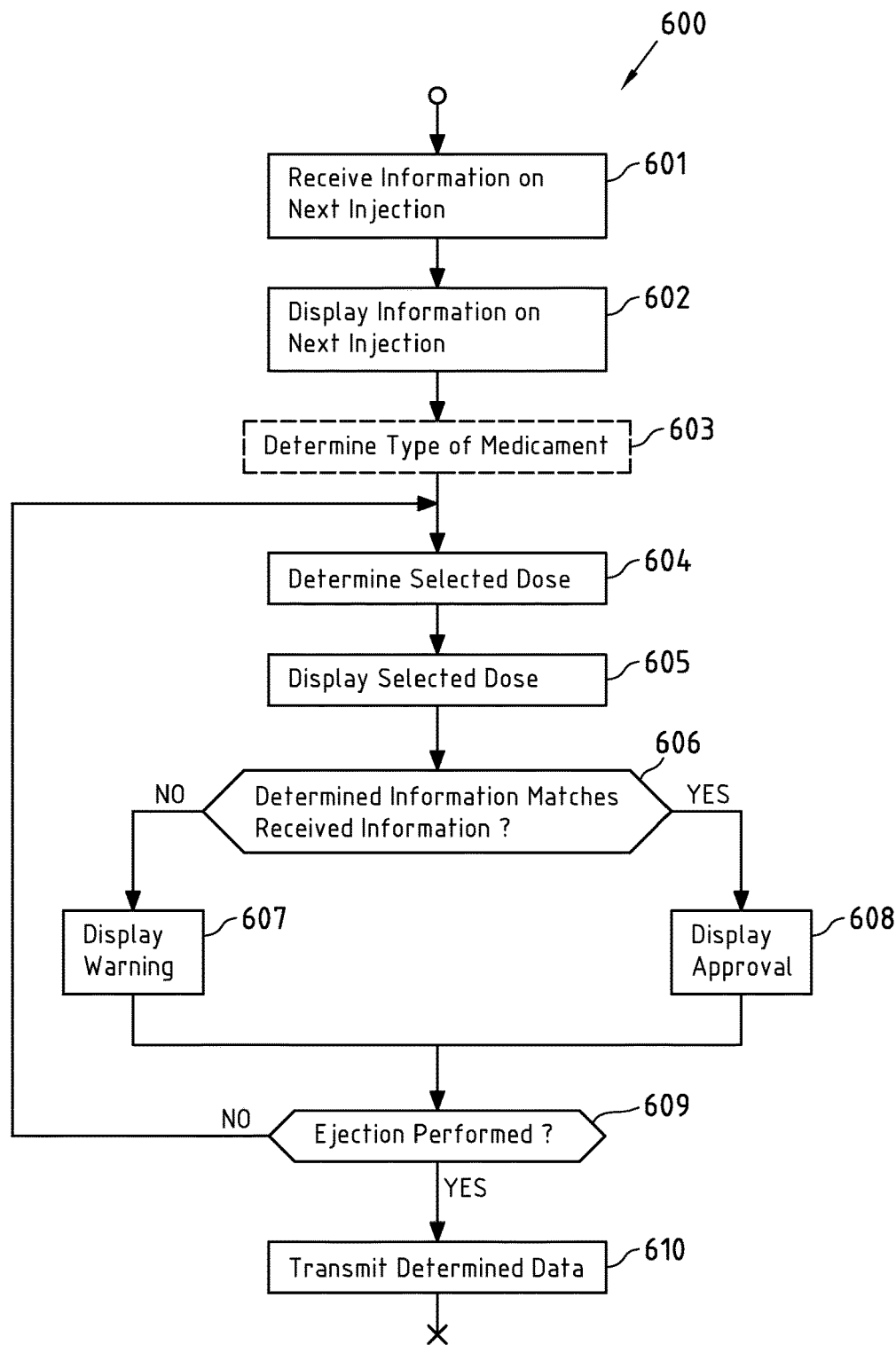
FIG. 5b: a flowchart of a further embodiment of a method according to the present invention.
Figure 5C:
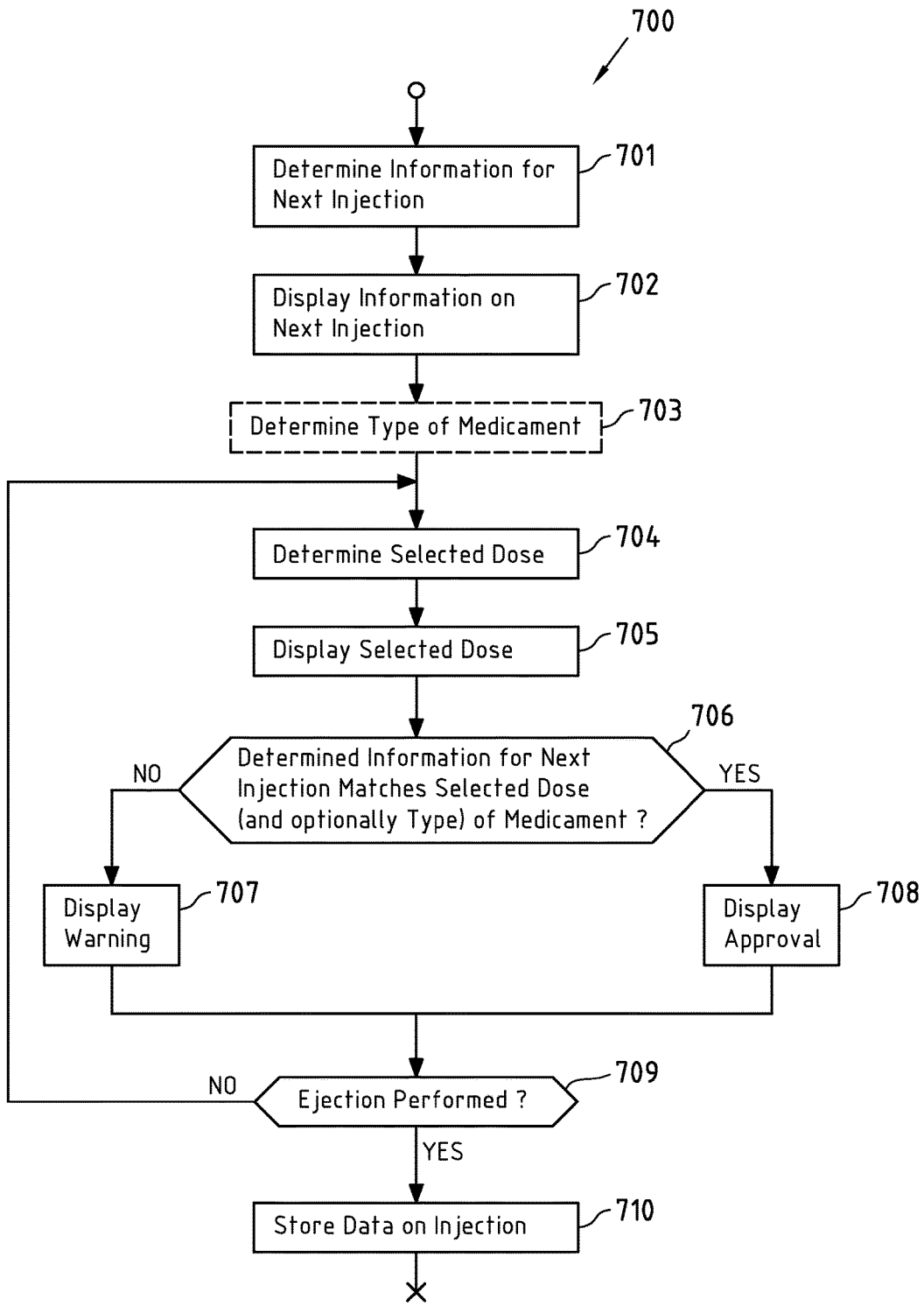
FIG. 5c: a flowchart of a further embodiment of a method according to the present invention.

FIGS. 5a-5c are flowcharts of embodiments of methods according to the present invention. These methods may for instance be performed by processor 24 of supplementary device 2 (see FIGS. 2b and 4), but also by a processor of supplementary device 3 of FIG. 2b, and may for instance be stored in program memory 240 of supplementary device 2, which may for instance take the shape of tangible storage medium 60 of FIG. 6.

FIG. 5a shows method steps that are performed in scenarios as shown in FIGS. 3a and 3b, where information read by supplementary device 41 from injection device 40 is provided to blood glucose monitoring system 42 or 42' without receiving information back from blood glucose monitoring system 42 or 42'.

The flowchart 500 starts for instance when the supplementary device is turned on or is otherwise activated.

In a step 501, a type of medicament, for example insulin, provided by the injection device is determined, for instance based on colour recognition or based on recognition of a code printed on injection device or a component thereof as already described above. Detection of the type of medicament may not be necessary if a patient always takes the same type of medicament and only uses an injection device with this single type of medicament. Furthermore, determination of the type of medicament may be ensured otherwise (e.g. by the key-recess pair shown in FIG. 4 that the supplementary device is only useable with one specific injection device, which may then only provide this single type of medicament).

In a step 502, a currently selected dose is determined, for instance by OCR of information shown on a dosage window of injection device as described above. This information is then displayed to a user of the injection device in a step 503, this may however also be optional.

In a step 504, it is checked if an ejection has taken place, for instance by sound recognition as described above. Therein, a prime shot may be differentiated from an actual injection (into a creature) either based on respectively different sounds produced by the injection device and/or based on the ejected dose (e.g. a small dose, for instance less than a pre-defined amount of units, e.g. 4 or 3 units, may be considered to belong to a prime shot, whereas larger doses are considered to belong to an actual injection).

If an ejection has taken place, the determined data, i.e. the selected dose and—if applicable—the type of medicament (e.g. insulin), is transmitted to another device, for instance a blood glucose monitoring system. If a differentiation has been made concerning the nature of the ejection, for instance if the ejection was performed as a prime shot or as an actual injection, this information may also be transmitted.

Otherwise, steps 502 and 503 are repeated.

After transmission of the data, the flowchart 500 terminates.

FIG. 5b shows method steps that are performed in scenarios as shown in FIGS. 3a and 3b, where information read by supplementary device 41 from injection device 40 is provided to blood glucose monitoring system 42 or 42' and information is also received back from blood glucose monitoring system 42 or 42'.

In flowchart 600, in a step 601, information relevant for a next injection (e.g. a proposal for a type and/or dose of a medicament (e.g. insulin) to be injected by a patient next) is received at the supplementary device, for instance from a blood glucose monitoring system.

In a step 602, this information is displayed to a user of the supplementary device, for instance to inform the user on the details of the next dose to be injected.

After a type of medicament (e.g. insulin) has been optionally determined (step 603), and also a selected dose has been determined (step 604) and displayed (step 605), in a step 606, it is checked if the determined information (selected dose and optionally the type of medicament) matches the information received in step 601. If this is the case, an approval is displayed in step 608. Otherwise, in step 607 a warning is displayed that the selected dose does not yet match the proposed dose.

In step 609, it is then checked if an ejection has been performed, and if this is the case, the determined data is transmitted (e.g. to a blood glucose monitoring system), for instance with further information on the nature of the ejection (prime shot or actual injection), and otherwise, steps 604-608 are repeated.

Therein, it is noted that steps 603, 604, 605, 609 and 610 of flowchart 600 correspond to steps 501-505 of flowchart 500 of FIG. 5a, with the explanations and examples given there also applying here.

FIG. 5c shows method steps that are performed in scenarios as shown in FIGS. 3c and 3d, where information read by supplementary device 41' or 41" from injection device 40 is processed by supplementary device 41' or 41" itself, for instance to perform blood glucose monitoring.

In a step 701 of flowchart 700, information related to a next injection (e.g. type and/or dose of the medicament (e.g. insulin)) is determined by the supplementary device, for instance based on information on a current blood glucose level either determined by the blood glucose meter comprised in the supplementary device itself (see FIG. 3d) or received from an external blood glucose meter (see FIG. 3c).

In a step 702, this information is then displayed via a display unit of the supplementary device.

After a type of medicament (e.g. insulin) has been optionally determined (step 703), and also a selected dose has been determined (step 704) and displayed (step 705), in a step 706, it is checked if the determined information from steps 703 and 704 (selected dose and optionally the type of medicament) matches the information determined in step 701. If this is the case, an approval is displayed in step 708. Otherwise, a warning is displayed in step 707 that the selected dose does not yet match the proposed dose.

In step 709, it is then checked if an ejection has been performed, and if this is the case, the determined data is stored (for instance in a logbook, for instance as a basis for later blood glucose monitoring processing), for instance together with further information on the nature of the ejection (prime shot or actual injection), and otherwise, steps 704-708 are repeated.

Therein, it is noted that steps 703, 704, 705 and 709 of flowchart 700 correspond to steps 501-505 of flowchart 500 of FIG. 5a, with the explanations and examples given there also applying here.

Figure 5D:
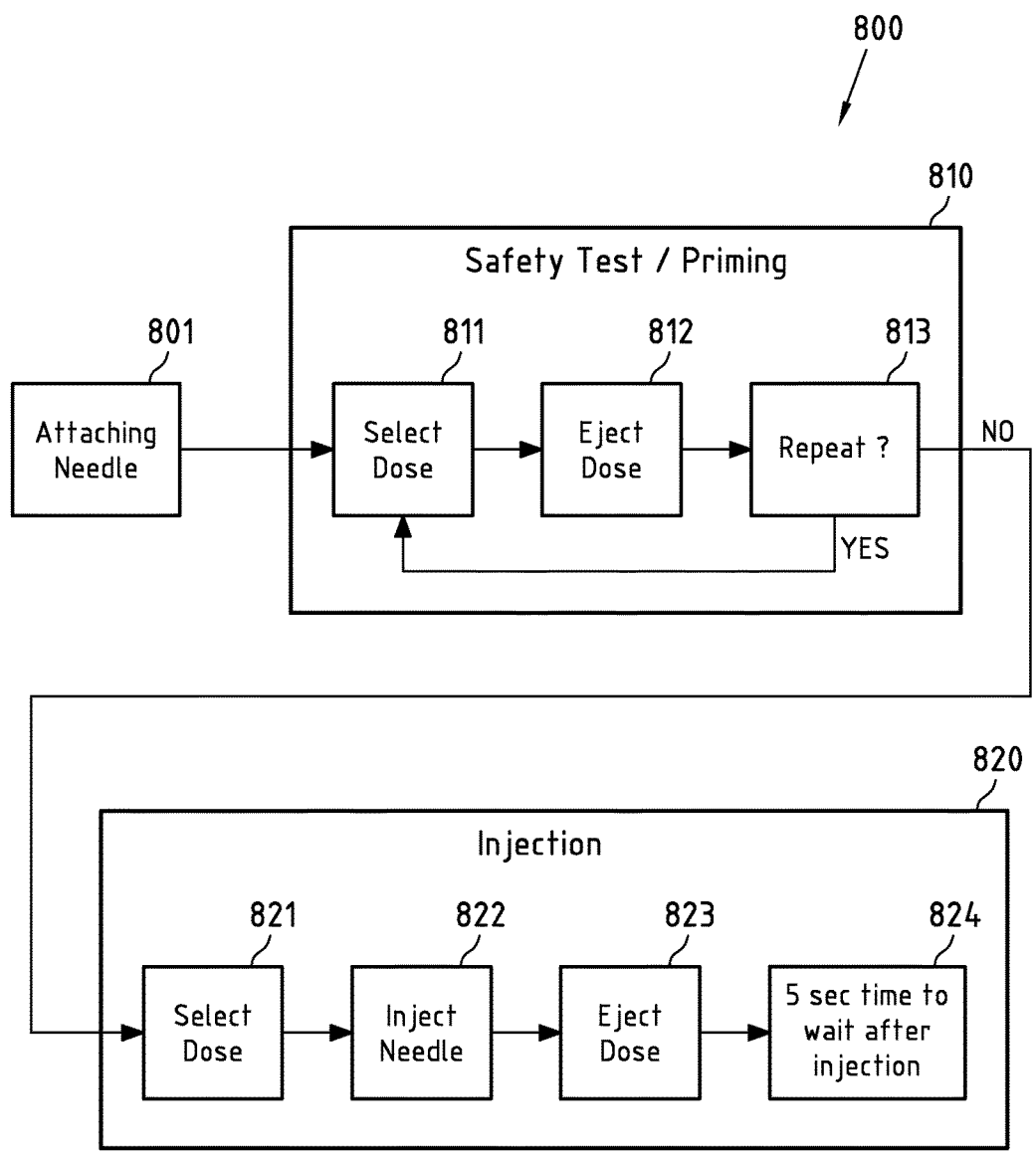
FIG. 5d: a typical application sequence of the injection device of FIG. 1.

FIG. 5d shows a typical application sequence of injection device 1, for instance Applicant's Solostar® insulin injection pen.

For injection device 1, a safety test 810 (i.e. priming) is required before the actual injection procedure 820.

After affixing the needle 15 to the injection device 1 in a step 801, the user is required to select a dose of two units to be ejected by injection device 1 in a step 811. An insulin dose can be selected by turning dosage knob 12. Step 811 is the first step of the safety test 810.

In a step 812, the selected dose is ejected so that normally insulin emerges from the tip of the needle 15 affixed to the injection device 1.

In a step 813, it is determined whether or not the safety test 810 must be repeated. The safety test 810 must be repeated if no insulin emerges from the tip of the needle in step 812.

Otherwise in a step 821, a dose to be injected by the injection device 1 is selected. An insulin dose can be selected by turning dosage knob 12. This is the first step of the actual injection procedure 820.

In a step 822, the needle 15 is injected into the body.

In a step 823, the selected dose is ejected by the injection device 1 and injected into the body.

In a step 824, the user waits for about 5 seconds after the actual injection.

Apparently, the safety test 810 is indistinguishable from the selection of the dose for the actual injection (see steps 811 and 821) and successive injection (see steps 812 and 823) as the acoustical and optical signals are identical. If the selected doses determined by the supplementary device 2 are for instance stored in a logbook, it is however useful to distinguish between both situations.

Exemplary time steps of the application sequence of injection device 1 (e.g. Applicant's Solostar® insulin injection pen) may be the following:

Time difference between dose dialing (e.g. turning the dosage knob) and injection/ejection>3 seconds Time for injection/ejection 1-30 seconds Time difference after the injection/ejection before dosage knob 12 is turned again>3 seconds Time difference after the safety test/priming before dosage knob 12 is turned again>1 second.

Accordingly, objectives for determining the selected dose are for instance:

Dialling the dose/turning the dosage knob is monitored with a high repetition rate.

The time difference between dialing the dose/turning the dosage knob and displaying the corresponding number is minimized.

If the selected dose/the dosage knob remains unchanged for more than 3 seconds, the corresponding number (e.g. a number visible through dosage window 13) is used as the number of units selected for injection.

If the selected dose/dosage knob reads zero for more than 0.1 seconds, the number is returned.

Figure 5E:
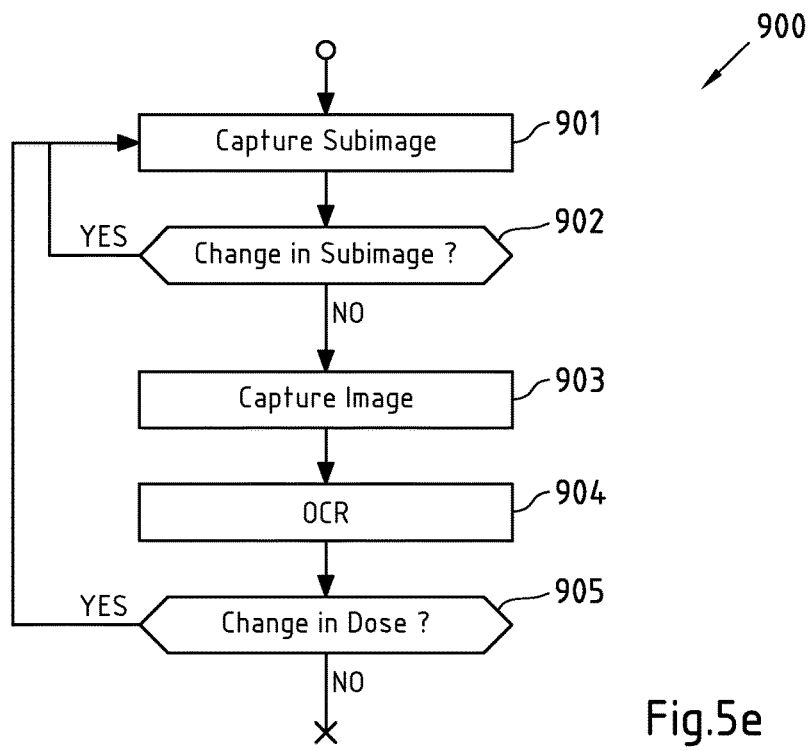
FIG. 5e: a flowchart of a further embodiment of a method according to the present invention.

FIG. 5e shows in more detail exemplary method steps that are performed when the selected dose is determined based on the use of optical sensors only. For instance, these steps may be performed in steps 502, 604 and 704 of FIGS. 5a-c.

In a step 901, a sub-image is captured by an optical sensor such as optical sensor 25 of supplementary device 2. The captured sub-image is for instance an image of at least a part of the dosage window 13 of injection device 1, in which a currently selected dose is displayed (e.g. by means of numbers and/or a scale printed on the sleeve 19 of injection device 1, which is visible through the dosage window 13). For instance, the captured sub-image may have a low resolution and/or only show a part of the part of sleeve 19 which is visible through dosage window 13. For instance, the captured sub-image either shows the numbers or the scale printed on the part of sleeve 19 of injection device 1 which is visible through dosage window 13.

After capturing an image, it is, for instance, further processed as follows:

Division by a previously captured background image;

Binning of the image(s) to reduce the number of pixels for further evaluations;

Normalization of the image(s) to reduce intensity variations in the illumination;

Sheering of the image(s); and/or

Binarization of the image(s) by comparing to a fixed threshold.

Several or all of these steps may be omitted if applicable, for instance if a sufficiently large optical sensor (e.g. a sensor with sufficiently large pixels) is used.

In a step 902, it is determined whether or not there is a change in the captured sub-image. For instance, the currently captured sub-image may be compared to the previously captured sub-image(s) in order to determine whether or not there is a change. Therein, the comparison to previously captured sub-images may be limited to the sub-image of the previously captured sub-images that was captured immediately before the current sub-image was captured and/or to the sub-images of the previously captured sub-images that were captured within a specified period of time (e.g. 0.1 seconds) before the current sub-image was captured. The comparison may be based on image analysis techniques such as pattern recognition performed on the currently captured sub-image and on the previously captured sub-image. For instance, it may be analyzed whether the pattern of the scale and/or the numbers visible through the dosage window 13 and shown in the currently captured sub-image and in the previously captured sub-image is changed. For instance, it may be searched for patterns in the image that have a certain size and/or aspect ratio and these patterns may be compared with previously saved patterns.

Steps 901 and 902 may correspond to a detection of a change in the captured image. If it is determined in step 902 that there is a change in the sub-image, step 901 is repeated. [admin3]

Otherwise in a step 903, an image is captured by an optical sensor such as optical sensor 25 of supplementary device 2. The captured image is for instance an image of the dosage window 13 of injection device 1, in which a currently selected dose is displayed (e.g. by means of numbers and/or a scale printed on the sleeve 19 of injection device 1, which is visible through the dosage window 13). For instance, the captured image may have a resolution being higher than the resolution of the captured sub-image. The captured image at least shows the numbers printed on the sleeve 19 of injection device 1 which are visible through the dosage window 13.

In a step 904, an optical character recognition (OCR) is performed on the image captured in step 903 in order to recognize the numbers printed on the sleeve 19 of injection device 1 and visible through the dosage window 13, because these numbers correspond to the (currently) selected dose. In accord to the recognized numbers, the selected dose is determined, for instance by setting a value representing the selected dose to the recognized numbers.

In a step 905, it is determined whether or not there is a change in the determined selected dose and, optionally, whether or not the determined selected dose does not equal zero. For instance, the currently determined selected dose may be compared to the previously determined selected dose(s) in order to determine whether or not there is a change. Therein, the comparison to previously determined selected dose(s) may be limited to the previously determined selected dose(s) that were determined within a specified period of time (e.g. 3 seconds) before the current selected dose was determined. If there is no change in the determined selected dose and, optionally, the determined selected dose does not equal zero, the currently determined selected dose is returned/forwarded for further processing (e.g. to processor 24).

Thus, the selected dose is determined if the last turn of the dosage knob 12 is more than 3 seconds ago. If the dosage knob 12 is turned within or after these 3 seconds and the new position remains unchanged for more than 3 seconds, this value is taken as the determined selected dose.

Figure 5F:
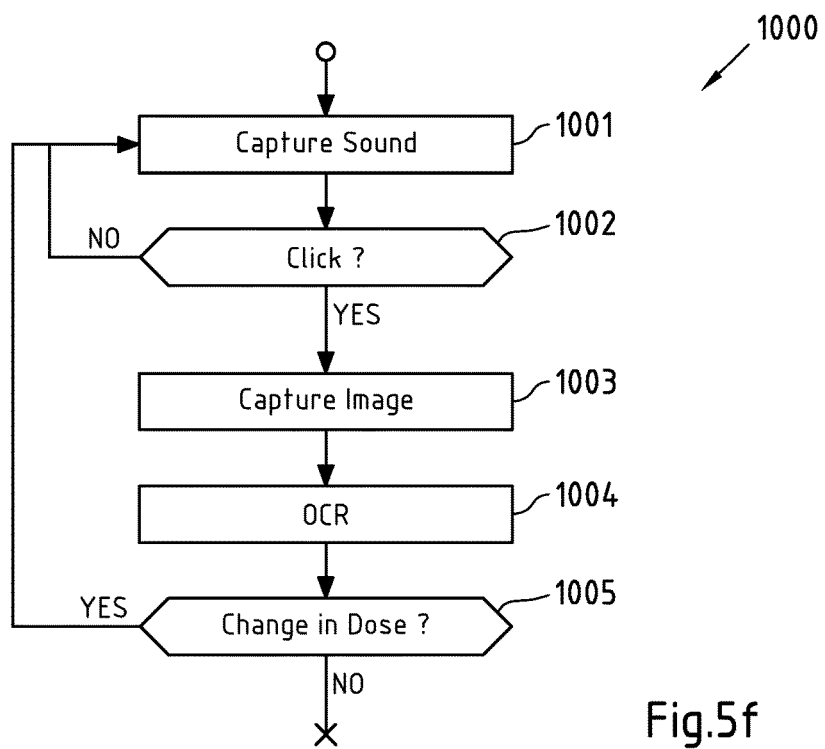
FIG. 5f: a flowchart of a further embodiment of a method according to the present invention.

FIG. 5f shows in more detail method steps that are performed when the selected dose is determined based on the use of acoustical and optical sensors. For instance, these steps may be performed in steps 502, 604 and 704 of FIGS. 5a-c.

In a step 1001, a sound is captured by an acoustical sensor such as acoustical sensor 27 of supplementary device 2.

In a step 1002, it is determined whether or not the captured sound is a click sound. The captured sound may for instance be a click sound that occurs when a dose is dialed by turning dosage knob 12 of injection device 1 and/or when a dose is ejected/injected by pressing injection button 11, and/or when a prime shot is performed. If the captured sound is not a click sound, step 1001 is repeated.

Otherwise in a step 1003, an image is captured by an optical sensor such as optical sensor 25 of supplementary device 2. Step 1003 corresponds to step 903 of flowchart 900.

In a step 1004, an OCR is performed on the image captured in step 1003. Step 1004 corresponds to step 904 of flowchart 900.

In a step 1005, it is determined whether or not there is a change in the determined selected dose and, optionally, whether or not the determined selected dose does not equal zero. Step 1005 corresponds to step 905 of flowchart 900.

There might be a slight advantage of the acoustic approach shown in FIG. 5f when it comes to power consumption of the supplementary device, because permanently capturing images or sub-images as shown in FIG. 5e typically is more power consuming than listening to an acoustical sensor such as a microphone.

Figure 5G:
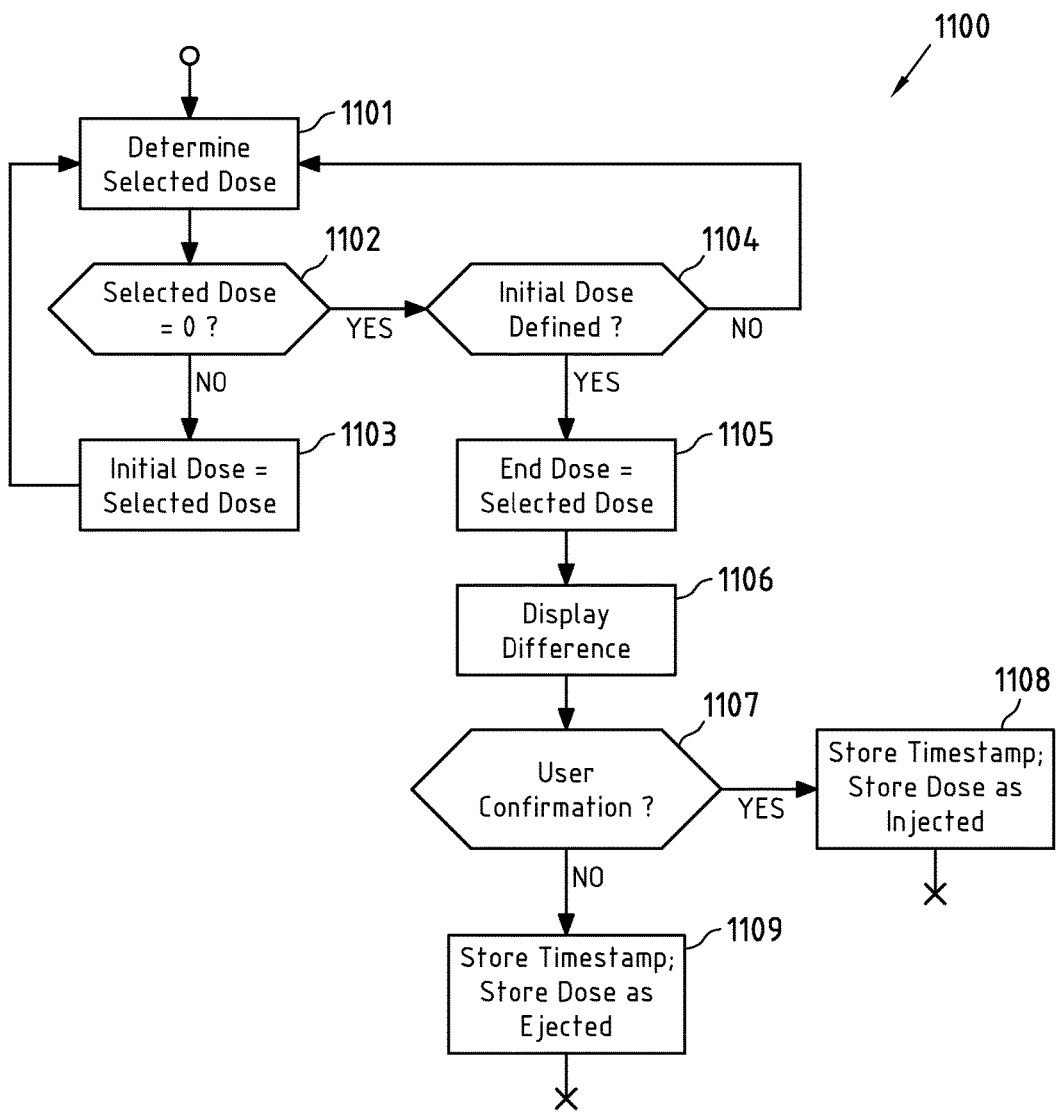
FIG. 5g: a flowchart of a further embodiment of a method according to the present invention.

FIG. 5g shows in more detail method steps that are performed when the determined selected dose is stored in a logbook.

In a step 1101 the currently selected dose is determined, for instance in accord with the steps of flowcharts 900 or 1000.

In a step 1102, it is determined whether the determined selected dose equals zero. If it does not equal zero, the value "initial dose" is set to the value of the determined selected dose in a step 1103.

Otherwise in a step 1104, is determined whether or not the value "initial dose" has been defined previously. If it has not been defined previously, step 1101 is repeated.

Otherwise in a step 1105, the value "end dose" is set to the value of the determined selected dose.

In a step 1106, the difference between the values "initial dose" and "end dose" is displayed and, in a step 1107, the user is asked to confirm the difference as injected.

If the user confirms the difference as injected, in a step 1108, the difference is stored in the logbook as being injected, optionally a timestamp is added to the corresponding entry in the logbook.

If the user does not confirm the difference to be injected, in a step 1109, the difference is stored in the logbook as being ejected, optionally a timestamp is added to the corresponding entry in the logbook.

Thus, the "initial dose" is for instance detected if the last turn of the dosage knob is more than 3 seconds ago. If the dosage knob is turned within or after these 3 seconds and the new position remains unchanged for more than 3 seconds, the correspondingly detected value is taken as "initial dose". If the determined selected dose equals zero and an "initial dose" other than zero was defined, the value of "initial dose" is displayed and the user is asked to confirm the displayed value as being injected.

A user confirmation of the selected dose in step 1107 may be necessary to distinguish between the dose ejected during the safety test (priming) and the actually injected dose.

The safety test is mostly a mandatory step in the application sequence. A distinction between the dose ejected during the priming and the actually injected dose can be implemented in different ways:

1. The user activates the supplementary device 2 after the safety test 810 but before the actual injection procedure 820. However, as the supplementary device 2 blocks the view of the dosage window 13 the user cannot check before the safety test 810 the initially selected dose and during the safety test 810 whether the selected dose is two units and after the safety test whether the dose is set to zero again. Furthermore, the dose ejected during the priming cannot be stored to monitor the amount of insulin left in the cartridge.

2. The user activates the supplementary device 2. The first determined selected dose is shown on the display, but it is not stored in the logbook as injected. Any further selected and ejected dose is stored as injected.

However, for users who either skip the priming or add two units to the selected dose that they would like to eject prior to the injection of the needle, the supplementary device 2 does not store the injected dose correctly. Users who repeat the priming create incorrect dosage recordings.

3. The user activates the supplementary device 2, the first determined selected dose is compared to the value two and if true, it is not stored. Any further dose is stored.

However, for users who either skip the priming or add two units to the selected dose that they would like to eject prior to the injection of the needle, the supplementary device 2 does also not store the injected dose correctly. Users who repeat the priming also create incorrect recordings. If the users does not stick to the value of two units for the safety test this might also result in incorrect recordings.

4. The user activates the supplementary device 2. As long as the determined selected dose is equal to the value two, the dose is not stored. Any further dose is stored.

However, for users who add two units to the selected dose that they would like to eject prior to the injection of the needle, the supplementary device 2 does not record the injected dose correctly. An insulin dose of two will not be properly recorded.

5. The user activates the supplementary device 2. The dose is recorded for the safety test 810 and for the actual injection 820. The dose is only stored as being injected if the user acknowledges the determined selected dose(s) (e.g. the difference of "initial value" and "end value") as correct and/or as injected. Otherwise, the determined selected dose(s) may be corrected and/or stored as ejected to monitor the amount of insulin left in the cartridge.

Only this implementation of an acknowledgement by the user may be versatile enough to cover the many possible actions of the user during the application sequence. An acknowledgement of the user that the determined selected dose is correct and that the dose was really injected into the body additionally closes loopholes that exist if the sequence of user action differs substantially from what is shown in FIG. 5d.

For instance, there exist several application sequences that may lead to an incorrect determination and storage of the selected dose, when the determined selected dose is not acknowledged:

For instance, when the user dials a dose, waits for a specified period of time (e.g. 3 seconds) and turns the dosage knob to zero without ejecting/injecting the dialed dose, the selected dose may however be determined as ejected/injected.

For instance, when the user dials a dose, waits for a specified period of time (e.g. more than 3 seconds), injects the dialed dose partially, waits for a specified period of time (e.g. more than 3 seconds), injects the remaining part of the dialed dose, the determined selected dose may be smaller than the injected dose.

For instance, when the user dials a dose, waits less than a specified period of time (e.g. less than 3 seconds), injects the dialed dose entirely, the selected dose may not be determined. When the user repeats this sequence, the determined selected dose may be smaller than the injected dose.

For instance, if the user dials a dose, waits for a specified period of time (e.g. 3 seconds), injects the dialed dose entirely, waits less than a specified period of time (e.g. less than 1 seconds) before repeating this sequence, the determined selected dose may be smaller than the injected dose.

To make it obvious for a user that he is expected to wait for a specified period of time, display 21 could flash while displaying the determined selected dose for the specified period of time and switch to a non-flashing/permanent mode thereafter.

Figure 6:
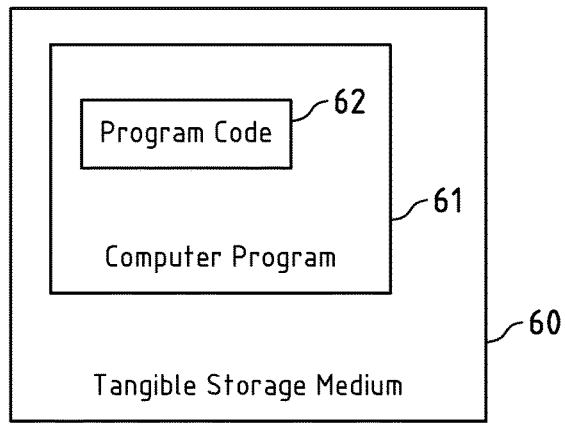
FIG. 6: a schematic illustration of a tangible storage medium 60 according to an embodiment of the present invention.

FIG. 6 is a schematic illustration of a tangible storage medium 60 (a computer program product) that comprises a computer program 61 with program code 62 according to an embodiment of the present invention. This program code may for instance be executed by processors contained in the supplementary device, for instance processor 24 of supplementary device 2 of FIGS. 2a and 4, but also of a processor of supplementary device 3 of FIG. 2b. For instance, storage medium 60 may represent program memory 240 of supplementary device 2 of FIG. 4. Storage medium 60 may be a fixed memory, or a removable memory, such as for instance a memory stick or card.

Figure 7:
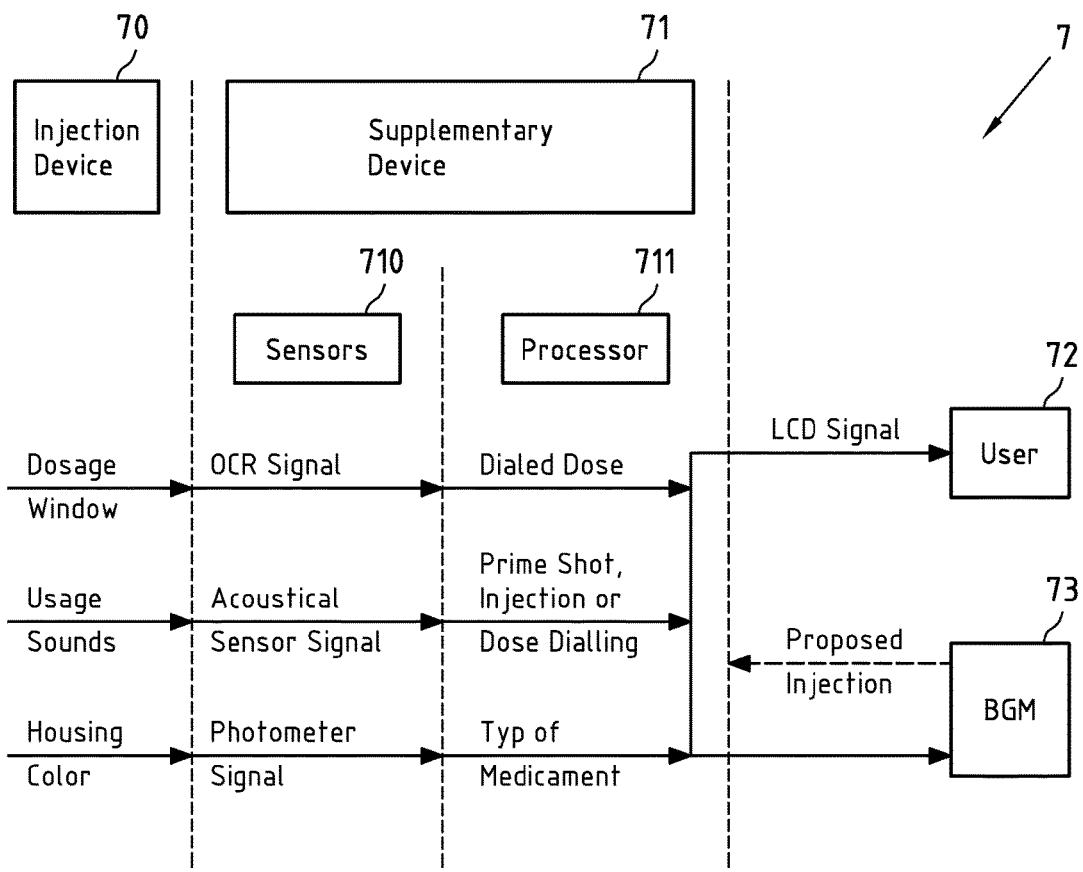
FIG. 7: an information sequence chart that illustrates an information flow between various devices according to an embodiment of the present invention.

Finally, FIG. 7 is an information sequence chart 7 that illustrates the flow of information between various devices (e.g. the injection device 1 and the supplementary device 2 of FIG. 4 in a scenario as depicted in FIG. 3a or 3b) according to an embodiment of the present invention.

A condition and/or use of injection device 70 affects an appearance of its dosage window, sounds generated by injection device 70 and a colour of the housing. This information is transformed by sensors 710 of supplementary device 71 into an OCR signal, an acoustic sensor signal and a photometer signal, respectively, which are in turn transformed into information on the dialed dose, on an injection/dialling operation and on the type of insulin by a processor 711 of supplementary device 71, respectively. This information is then provided by supplementary device 70 to a blood glucose monitoring system 73, and may also be displayed to a user 72 via an LCD signal. Furthermore, information related to a proposed next injection is optionally transmitted from blood glucose monitoring system 73 to supplementary device 71 (and may also be displayed to user 72).

As described in detail above, embodiments of the present invention allow connection of a standard injection device, in particular an insulin device, with a blood glucose monitoring system in a useful and productive way.

Embodiments of the present invention introduce a supplementary device to allow for this connection, assuming the blood glucose monitoring system has wireless or other communication capabilities. Other embodiments show that the blood glucose monitoring system is included into the supplementary device.

The benefits from the connection between the blood glucose monitoring and an insulin injection device are inter alia the reduction of mistakes by the user of the injection device and a reduction of handling steps—no more manual transfer of the injected insulin unit to a blood glucose monitoring is required, in particular to a blood glucose monitoring system with functionality of providing guidance for the next dose based on the last dose injected and latest blood glucose values.

As described with reference to exemplary embodiments above, when a user/patient gets a new insulin pen, the user attaches the supplementary device to the pen. The supplementary device reads out the injected dose and transfers it to a blood glucose monitoring system with insulin titration capabilities. The blood glucose monitoring system may also transmit the recommended next dose to be taken to the supplementary device e.g. to check whether the recommended dose is identical with the injected dose or not. For patients taking multiple insulins, the supplementary device recognizes the device structure to the insulin type and may also transmit this piece of information to the blood glucose monitoring system.

In an example embodiment, the information shown on a display, for example LCD display 21 of FIGS. 2a and 4 or display 32 of FIG. 2b, may also converted to a sound signal played to a user through a speaker, for example by a text-to-speech functionality implemented by processor 24. Thus, a user with impaired vision may have improved access to the information of supplementary devices 2 or 3, such as a dialed dose, a recommended dose, a recommended time for administration and/or the like.

When using embodiments of the present invention, the user inter alia has the following advantages:
The user can use the most convenient disposable insulin injector.
The supplementary device is attachable and detachable (reusable).
Injected dose information may be transferred to the blood glucose monitoring system automatically (no more transfer mistakes).
Improved dose guidance may result from this as the blood glucose monitoring system calculates the dose to be taken.
Keeping of a manual data logbook may not be needed any more.
Furthermore, when deploying the supplementary device proposed by the present invention, patients may also be reminded of injecting their next dose by receiving an alarm signal, for instance, after an appropriate time after a first dose of a medicament (for instance insulin or heparin) has been injected.
Injected dose information may be transferred to any computerized system, for instance as input for any dose calculation or any other applicable therapeutic guidance calculation, or for the creation of an alarm signal, for instance to remind the user of taking the next dose.

The term "medicament", as used herein, means a pharmaceutical formulation containing at least one pharmaceutically active compound,
wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound,
wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis,
wherein in a further embodiment the pharmaceutically active compound comprises at least one peptide for the treatment and/or prophylaxis of diabetes mellitus or complications associated with diabetes mellitus such as diabetic retinopathy,
wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically Acceptable Solvates are for Example Hydrates.

The invention has been described above by means of embodiments, which shall be understood to be non-limiting examples only. In particular, it should be noted that there are alternative ways and variations which are obvious to a skilled person in the art and can be implemented without deviating from the scope and spirit of the appended claims.

It should also be understood that the sequence of method steps in the flowcharts presented above is not mandatory, also alternative sequences may be possible. All functional blocks of apparatuses shall also be understood as a disclosure of an according method step, and similarly, each method step shall be considered as a disclosure of an according functional unit of an apparatus. It is well understood that the method steps and functional components can be implemented in various ways either in hardware only, or in software only, or in a combination of hard- and software.

In particular, the following embodiments of aspects of the present invention are to be disclosed.

Embodiment 1

An apparatus (2, 3), comprising
a mating unit (20-1, 20-2; 31) for releasably attaching the apparatus (2) to a medical device (1) or for releasably receiving at least a part of the medical device (1), and
one or more optical sensors (25, 26) and/or one or more acoustical sensors (27) for determining information related to a condition and/or use of the medical device (1).

Embodiment 2

The apparatus (2, 3) according to embodiment 1, wherein the one or more optical sensors (25, 26) comprise at least one optical sensor (25) configured to capture an image of an information-bearing or information-displaying (13) part of the medical device (1).

Embodiment 3

The apparatus (2, 3) according to embodiment 2, wherein the apparatus (2, 3) is configured to recognize characters from the captured image.

Embodiment 4

The apparatus (2, 3) according to any of the embodiments 1-3, wherein the one or more optical sensors (25, 26)

comprise at least one optical sensor (26) configured to capture information representative of a colour of at least a part (10) of the medical device (1) or to determine a colour of at least a part of the medical device (1).

Embodiment 5

The apparatus (2, 3) according to embodiment 4, wherein the apparatus (2, 3) is configured to recognize a colour of the part (10) of the medical device (1) from the captured information.

Embodiment 6

The apparatus (2, 3) according to any of the embodiments 1-5, wherein the one or more acoustical sensors (27) comprise at least one acoustical sensor (27) configured to capture a sound produced when the medical device (1) is used.

Embodiment 7

The apparatus (2, 3) according to embodiment 6, wherein the apparatus (2, 3) is configured to recognize, from the captured sound, at least an ejection of a medicament performed with the medical device (1).

Embodiment 8

The apparatus (2, 3) according to any of the embodiments 1-7, further comprising a display unit (21) for displaying information representative of at least a part of the determined information.

Embodiment 9

The apparatus (2, 3) according to any of the embodiments 1-8, further comprising an interface (28) configured to provide the determined information to another device 42, 42') via a wired or wireless connection.

Embodiment 10

The apparatus (2, 3) according to any of the embodiments 1-9, further comprising an interface (28) configured to receive information indicative of a type and/or dose of medicament to be ejected.

Embodiment 11

The apparatus according to any of the embodiments 1-10, further comprising a processor (24) for determining a proposal of a type and/or dose of a medicament to be ejected by the medical device.

Embodiment 12

The apparatus according to any of the embodiments 1-11, further comprising a measurement unit (29) for measuring at least one parameter that is representative of a condition of a creature that is to receive a medicament ejectable by the medical device.

Embodiment 13

A system, comprising a medical device (1) and an apparatus (2, 3) according to any of the embodiments 1-12.

Embodiment 14

A method (500, 600, 700), comprising
determining, based on information captured by one or more optical sensors (25, 26) and/or one or more acoustical sensors (27), information related to a condition and/or use of a medical device (1), wherein the sensors (25, 26, 27) are comprised in an apparatus (2, 3) that further comprises a mating unit (20-1, 20-2; 31) for releasably attaching the apparatus (2) to the medical device (1) or for releasably receiving at least a part of the medical device (1).

Embodiment 15

A computer program (61), comprising instructions operable to cause a processor (24) to perform the method (500, 600, 700) of embodiment 14 when the computer program (61) is executed on the processor (24).

The invention claimed is:

1. A method of utilizing a supplementary device to determine information related to an injection device, the method comprising:
   activating a supplementary device; and
   determining whether an ejection has taken place, wherein determining whether the ejection has taken place comprises differentiating a prime shot from an actual injection based upon ejection sounds sensed by an acoustic sensor, and wherein a first ejection sound produced when performing the prime shot is differentiated acoustically from a second ejection sound produced by the actual injection.

2. The method of claim 1, further comprising in response to determining that the ejection has taken place, generating determined data and transmitting the determined data to another device or storing determined data in a memory of the supplementary device.

3. The method of claim 2, further comprising storing the determined data in a logbook.

4. The method of claim 2, further comprising receiving a user input confirming the determined data as correct before storing the determined data.

5. The method of claim 2, further comprising
   in response to determining that the ejection has taken place,
      transmitting at least one of selected dose data and medicament type data to another device.

6. The method of claim 1 further comprising determining a currently selected dose, wherein determining the currently selected dose comprises:
   capturing a sub-image by an optical sensor; and
   processing the sub-image.

7. The method of claim 6 wherein
   the step of processing the sub-image comprises the steps of
      dividing the image by a previously captured background image;
      binning of the sub-image to reduce a number of pixels;
      normalizing the sub-image to reduce intensity variations in the illumination;
      sheering of the sub-image and the previously captured background image; and
      comparing the sub-image and the previously captured background image to a fixed threshold.

8. The method of claim 7 further comprising the step of determining whether there is a change in the sub-image, wherein the step of determining whether there is a change in the sub-image comprises the step of
   comparing a currently captured sub-image to the previously captured sub image.

9. The method of claim 8 wherein, if it is determined that there is a change in the sub-image, the method further comprises the steps of:
  capturing the sub-image by an optical sensor; and
  processing the sub-image.

\* \* \* \* \*

UNITED STATES PATENT AND TRADEMARK OFFICE
CERTIFICATE OF CORRECTION

PATENT NO. : 10,391,235 B2
APPLICATION NO. : 14/791293
DATED : August 27, 2019
INVENTOR(S) : Michael Schabbach and Amit Kohli It is certified that error appears in the above-identified patent and that said Letters Patent is hereby corrected as shown below:

In the Claims

Column 32, Line 67, Claim 8, delete "sub image." and insert -- sub-image. --.

Signed and Sealed this
Tenth Day of December, 2019

Andrei Iancu
*Director of the United States Patent and Trademark Office*